(12) United States Patent
Sasikumar et al.

(10) Patent No.: US 7,030,113 B2
(45) Date of Patent: Apr. 18, 2006

(54) AMINOBENZIMIDAZOLES AS SELECTIVE MELANIN CONCENTRATING HORMONE RECEPTOR ANTAGONISTS FOR THE TREATMENT OF OBESITY AND RELATED DISORDERS

(75) Inventors: Thavalakulamgara K. Sasikumar, Edison, NJ (US); Duane A. Burnett, Bernardsville, NJ (US)

(73) Assignee: Schering Corporation, Kenilworth, NJ (US)

( * ) Notice: Subject to any disclaimer, the term of this patent is extended or adjusted under 35 U.S.C. 154(b) by 84 days.

(21) Appl. No.: 10/954,786

(22) Filed: Sep. 30, 2004

(65) Prior Publication Data

US 2005/0085488 A1   Apr. 21, 2005

Related U.S. Application Data

(60) Provisional application No. 60/508,027, filed on Oct. 2, 2003.

(51) Int. Cl.
*A61K 31/454*   (2006.01)
*A61K 31/496*   (2006.01)
*C07D 401/12*   (2006.01)
*C07D 403/12*   (2006.01)
*C07D 413/14*   (2006.01)

(52) U.S. Cl. .............. 514/234.5; 514/254.06; 514/322; 544/121; 544/370; 546/199

(58) Field of Classification Search ................ 544/121, 544/370; 546/199; 514/234.5, 254.06, 322
See application file for complete search history.

(56) References Cited

U.S. PATENT DOCUMENTS

| 5,908,830 | A | 6/1999 | Smith et al. |
|---|---|---|---|
| 2003/0212070 | A1 | 11/2003 | Schwink et al. |
| 2003/0216390 | A1 | 11/2003 | DeSimone et al. |
| 2004/0192693 | A1 | 9/2004 | Shwink et al. |
| 2004/0198731 | A1 | 10/2004 | Schwink et al. |
| 2004/0198732 | A1 | 10/2004 | Schwink et al. |
| 2004/0198733 | A1 | 10/2004 | Schwink et al. |

FOREIGN PATENT DOCUMENTS

| WO | 03/015769 | 2/2003 |
|---|---|---|
| WO | 03/59289 | 7/2003 |
| WO | 2004/011440 | 2/2004 |
| WO | 2004/031177 | 4/2004 |
| WO | WO-2004100875 | * 11/2004 |

OTHER PUBLICATIONS

Masako Shimada et al, Mice Lacking Melanin-Concentraling Hormone are Hypophagic and Lean, *Nature* 1998, 396: 670-674.
Beth Borowsky et al., Antidepressant, Anxiolytic and Anorectic Effects of a Melanin-Concentrating Hormone-1 Receptor Antagonists, *Nature Medicine* 2002, 8:825-828.
PCT International Search Report dated Sep. 30, 2004 for corresponding PCT Application No. PCT/US2004/032494 - 4 Pages.

* cited by examiner

*Primary Examiner*—Fiona T. Powers
(74) *Attorney, Agent, or Firm*—William Y. Lee

(57) ABSTRACT

The present invention discloses compounds of formula I

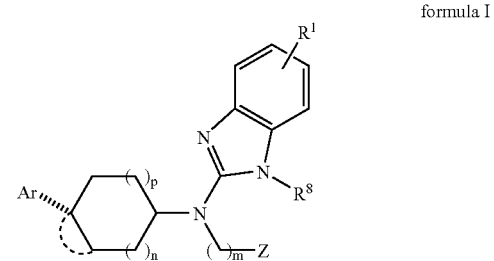

formula I wherein Ar, Z, m, n, p, $R^1$ and $R^8$ are herein defined, said compounds being novel antagonists for melanin-concentrating hormone (MCH), as well as methods for preparing such compounds. In another embodiment, the invention discloses pharmaceutical compositions comprising such MCH antagonists as well as methods of using them to treat obesity, metabolic disorders, eating disorders such as hyperphagia, and diabetes.

42 Claims, No Drawings

AMINOBENZIMIDAZOLES AS SELECTIVE MELANIN CONCENTRATING HORMONE RECEPTOR ANTAGONISTS FOR THE TREATMENT OF OBESITY AND RELATED DISORDERS

This application claims the benefit of priority of U.S. Ser. No. 60/508,027, filed Oct. 2, 2003.

FIELD OF THE INVENTION

This invention relates to antagonists for melanin-concentrating hormone (MCH) and their use in the treatment of metabolic and eating disorders, novel compounds having MCH receptor modulatory activity, pharmaceutical compositions containing one or more such modulators, methods of preparing such modulators and methods of using such modulators to treat obesity, diabetes and related disorders.

BACKGROUND OF THE INVENTION

MCH, a cyclic peptide, was first identified over a decade ago in teleost fish where it appears to regulate color change. More recently, MCH has been the subject of investigation for its possible role as a regulator of eating behavior in mammals. As reported by Shimada et al., *Nature*, Vol. 396 (17 Dec. 1998), pp. 670–673, MCH-deficient mice have reduced body weight and leanness due to hypophagia (reduced feeding). In view of their findings, it was suggested that antagonists of MCH may be effective for the treatment of obesity. U.S. Pat. No. 5,908,830 discloses a combination therapy for the treatment of diabetes or obesity involving the administration of a metabolic rate increasing agent and a feeding behavior modifying agent, an example of the latter being an MCH antagonist. Further, MCH receptor antagonists may also be useful in the treatment of depression and/or anxiety. Borowksy et al., *Nature Medicine*, 8, pp. 825–830 (1 Aug. 2002).

SUMMARY OF THE INVENTION

In one embodiment, this invention provides novel aryl-cycloalkyl aminobenzimidazole compounds having MCH antagonist activity. These compounds are represented by structural formula I:

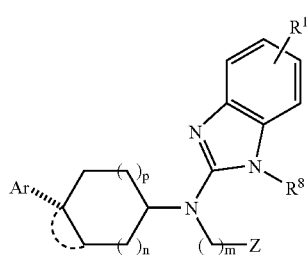

formula I or a pharmaceutically acceptable salt or solvate thereof, wherein the dashed line in

represents either
(i) an optional bond which may be present or absent, and if present, forms a double bond with the single bond it is adjacent to, or
(ii) —C($R^5R^8$)—, —C($R^5R^8$)—C($R^5R^8$)— or —C($R^{11}R^{12}$)—;

m is 1, 2, 3 or 4;
n is 0, 1 or 2;
p is 0, 1 or 2;
Ar is aryl, heteroaryl, $R^4$-substituted aryl or $R^4$-substituted heteroaryl;
Z is —$NR^5R^6$, —$NR^5C(O)R^3$, —$C(O)NR^5R^6$, —$NR^5C(O)NR^5R^6$, —$NR^5C(O)OR^3$, —$NR^5S(O_2)R^3$, —$S(O_2)NR^5R^6$, —$S(O_2)R^3$, —$C(O)R^3$, —$C(O)OR^6$, —OH, alkoxy,

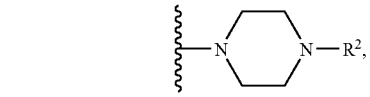

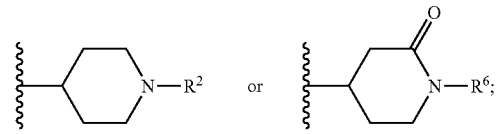

$R^1$ is 1 to 4 moieties, each $R^1$ is independently selected from the group consisting of hydrogen, —OH, halogen, alkyl, alkoxy, —$OCF_3$, —$CF_3$ or —CN, or two $R^1$ moieties on adjacent carbons of the cycloalkyl ring can be joined together to form a methylenedioxy or ethylenedioxy group;
$R^2$ is hydrogen, alkyl, $R^{10}$-substituted alkyl, cycloalkyl, $R^{10}$-substituted cycloalkyl, aralkyl, heterocyclyl, —$C(O)R^3$, —$S(O_2)R^3$ or —$C(O)NR^5R^6$;
$R^3$ is alkyl, aryl, aralkyl, heteroaryl, $R^4$-substituted aralkyl, $R^4$-substituted aryl or $R^4$-substituted heteroaryl;
$R^4$ is 1 to 5 moieties, each $R^4$ is independently selected from the consisting of hydrogen, heterocyclyl, $R^9$-substituted heterocyclyl, heterocyclylalkyl-, $R^9$-substituted heterocyclylalkyl, —OH, -alkoxy, —$OCF_3$, —CN, alkyl, halogen, —$NR^5R^6$, —$NR^5C(O)R^7$, —$C(O)NR^5R^6$, —$NR^5S(O_2)R^7$, —$S(O_2)NR^5R^6$, —$S(O_2)R^7$, —$COR^7$, —$C(O)OR^5$, —$CF_3$, -(alkylene)$NR^5R^6$, -(alkylene)$NR^6C(O)R^7$, -(alkylene)$NR^6S(O_2)R^7$, -(alkylene), —$NR^5C(O)NR^5R^6$, -(alkylene)$NR^5C(O)OR^7$, CHO, —C=($NOR^5$) and

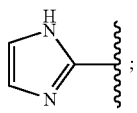

$R^5$ is hydrogen or alkyl;
$R^6$ is hydrogen, alkyl, aryl, aralkyl or heteroaryl;
$R^7$ is alkyl, aryl, aralkyl or heteroaryl;
$R^8$ is hydrogen or alkyl;
$R^9$ is alkyl, —OH or hydroxyalkyl;
$R^{10}$ is alkoxy, halogen, —C(O)NR$^5$R$^6$, —C(O)OR$^6$, —NR$^5$R$^6$ or —OH;
$R^{11}$ is hydrogen or halogen; and
$R^{12}$ is hydrogen or halogen.

This invention is also directed to pharmaceutical compositions for the treatment of metabolic disorders such as obesity, those disorders associated with obesity and eating disorders such as hyperphagia. In one aspect, this invention is directed to the method of treatment of metabolic disorders such as obesity, and eating disorders such as hyperphagia. Another embodiment includes a method of treating an eating disorder which comprises administering to a mammal in need of such treatment an amount of a first compound, said first compound being a compound of formula I; and a second compound, said second compound being an antiobesity and/or anorectic agent wherein the amounts of the first and second compounds result in the therapeutic desired effect. In another aspect, this invention is also directed to pharmaceutical compositions for the treatment of obesity which comprise an obesity treating amount of at least one compound of formula I, or a pharmaceutically acceptable salt or solvate of said compound and a pharmaceutically acceptable carrier.

DETAILED DESCRIPTION

The present invention relates to compounds that are represented by structural formula 1, or a pharmaceutically acceptable salt or solvate thereof, wherein the various moieties are as described above.

The dashed line portion of formula 1, as represented by

along with the accompanying single bond, together represent

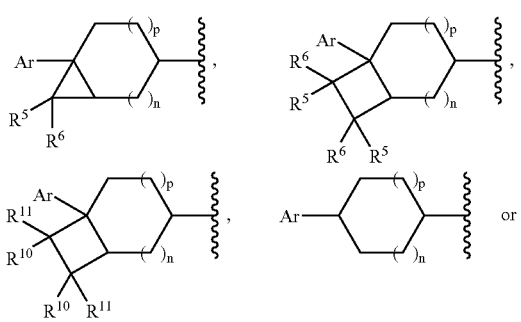

-continued

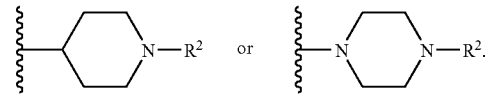

In one aspect of the invention are compounds of formula I where the dashed line in

is —CH$_2$—.

In addition, aspects of the invention include those compounds of formula I wherein m is 1 or 3.

Alternative aspects of the invention also include those compounds wherein n is 0 or 1.

Another aspect of the invention include those compounds of formula I wherein p is 1.

Another aspect of the invention include those compounds of formula I wherein Ar is R$^4$-substituted aryl or R$^4$-substituted heteroaryl.

Another aspect of the invention include those compounds of formula I wherein Z is

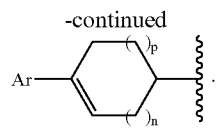

Another aspect of the invention include those compounds of formula I wherein R$^1$ is substituted on the parent ring as follows

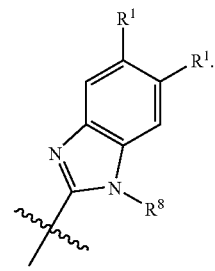

Another aspect of the invention include those compounds of formula I wherein R$^2$ is hydrogen, Boc, alkyl or —S(O$_2$)R$^3$.

Another aspect of the invention include those compounds of formula I wherein R$^3$ is alkyl.

Another aspect of the invention include those compounds of formula I wherein R$^4$ is -(alkylene)NR$^5$R$^6$, —CN, alkoxy, R$^9$-substituted heterocyclyl, CHO, —C=(NOR$^5$), heterocyclylalkyl-, R$^9$-substituted heterocyclylalkyl or halogen.

Another aspect of the invention include those compounds of formula I wherein R$^8$ is hydrogen or alkyl.

Another aspect of the invention include those compounds of formula I wherein R$^9$ is alkyl, —OH or hydroxyalkyl.

In addition, another aspect of the invention are compounds of formula I wherein the dashed line in

is —CH$_2$—; m is 1 or 3; n is 0 or 1; p is 1;

Ar is R$^4$-substituted aryl or R$^4$-substituted heteroaryl;

Z is

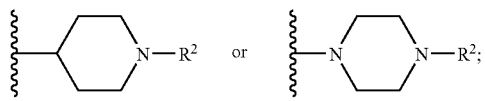

R$^1$ is substituted on the parent ring as follows

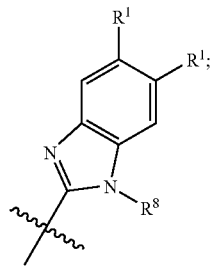

R$^2$ is hydrogen, Boc, alkyl or —S(O$_2$)R$^3$;

R$^3$ is alkyl;

R$^4$ is -(alkylene)NR$^5$R$^6$, —CN, alkoxy, R$^9$-substituted heterocyclyl, CHO, —C=(NOR$^5$), heterocyclylalkyl-, R$^9$-substituted heterocyclylalkyl or halogen;

R$^8$ is hydrogen or alkyl; and

R$^9$ is alkyl, —OH or hydroxyalkyl.

In addition, aspects of the invention include those compounds of formula I wherein the R$^1$ moieties are halogen or CF$_3$.

Alternative aspects of the invention also include those compounds of formula I wherein R$^2$ and R$^3$ are methyl.

Additional aspects of the invention include those compounds of formula I wherein R$^4$ is —CN, alkoxy, -(alkylene)NR$^5$R$^6$, R$^9$-substituted heterocyclyl, —C=(NOR$^5$), heterocyclylalkyl-, R$^9$-substituted heterocyclylalkyl- or halogen. Even more preferable are those compounds of formula I wherein R$^4$ is —CN, —CH$_2$N(CH$_3$)$_2$, Br, —C=NOCH$_3$,

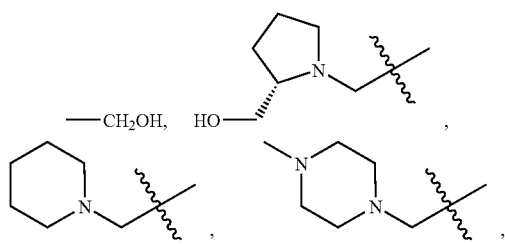

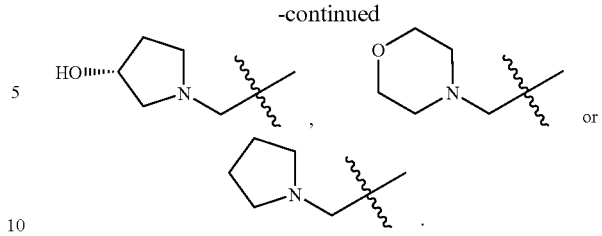

Another aspect of the invention include those compounds of formula I wherein R$^8$ is hydrogen or methyl.

Another aspect of the invention include those compounds of formula I wherein Z is

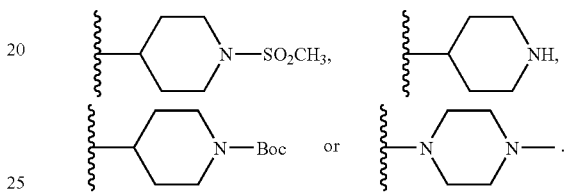

Another aspect of the invention include those compounds of formula I wherein the dashed line in

is —CH$_2$—; m is 3; n is 1; p is 1;

Ar is R$^4$-substituted aryl or R$^4$-substituted heteroaryl;

z is

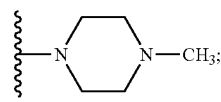

R$^1$ is halogen where said R$^1$ is substituted on the parent ring as follows

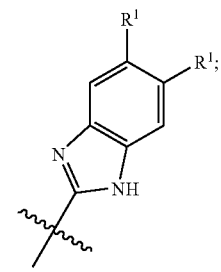

and

R$^4$ is —CN, alkoxy, -(alkylene)NR$^5$R$^6$, R$^9$-substituted heterocyclyl, —C=(NOR$^5$), heterocyclylalkyl-, R$^9$-substituted heterocyclylalkyl- or halogen.

Another aspect of the invention include those compounds of formula I wherein the dashed line in is

is —CH$_2$—; m is 1; n is 1; p is 1;
Ar is R$^4$-substituted aryl or R$^4$-substituted heteroaryl;
Z is

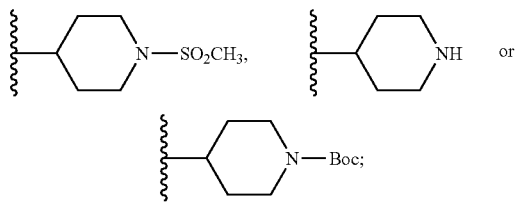

R$^1$ is halogen where said R$^1$ is substituted on the parent ring as follows

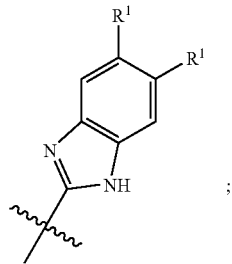

and
R$^4$ is —CN or halogen.

Another aspect of the invention include those compounds of formula I wherein the dashed line in

is —CH$_2$—; m is 3; n is 1; p is 1;
Ar is R$^4$-substituted aryl or R$^4$-substituted heteroaryl;
Z is

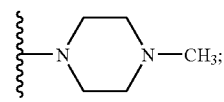

R$^1$ is halogen or CF$_3$, where said R$^1$ is substituted on the parent ring as follows

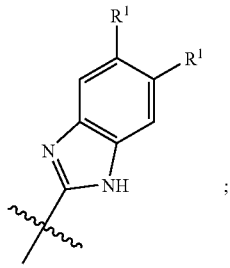

and
R$^4$ is —CN or halogen.

Still additional preferred embodiments of formula I include compounds selected from the group consisting of compounds of Examples 8a, 8b, 8c, 9a, 9b, 10a, 10b, 10c, 10d, 10e, 10f, 10g, 10h, 10i, 16a, 16b, 16c, 21, 22, 23, 24, 30a, 30b, 30c, 30d, 35a, 35b, 35c and 36, herein.

Other embodiments of the invention include methods of treatment with at least one compound of formula I wherein the eating disorder is hyperphagia and wherein the metabolic disorder is obesity.

Another embodiment is a method of treating a disorder associated with obesity comprising administering to a mammal in need of such treatment a therapeutically effective amount of at least one compound of formula I, or a pharmaceutically acceptable salt or solvate of said compound. Specific examples of disorders associated with obesity include but are not limited to type II diabetes, insulin resistance, hyperlipidemia or hypertension.

Another embodiment includes a method of treating an eating disorder which comprises administering to a mammal in need of such treatment an amount of a first compound, said first compound being a compound of formula I or a pharmaceutically acceptable salt or solvate of said compound; and a second compound, said second compound being an antiobesity and/or anorectic agent selected from the group consisting of a β$_3$ agonist, a thryomimetic agent, an anorectic agent and an NPY antagonist;

wherein the amounts of the first and second compounds result in the desired therapeutic effect (the treatment of obesity, obesity related disorders, metabolic and eating disorders).

Except where stated otherwise, the following definitions apply throughout the present specification and claims. These definitions apply regardless of whether a term is used by itself or in combination with other terms. Hence the definition of "alkyl" applies to "alkyl" as well as to the "alkyl" portions of "alkoxy", "cycloalkyl" and so forth.

As used above, and throughout the specification, the following terms, unless otherwise indicated, shall be understood to have the following meanings:

"Alkyl" means an aliphatic hydrocarbon group, which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means an alkyl group having about 1 to about 6 carbon atoms in the chain, which may be straight or branched. Non-limiting examples of suitable alkyl groups include methyl, ethyl, n-propyl, isopropyl, n-butyl, and t-butyl.

"Alkoxy" means an alkyl-O— group in which the alkyl group is as previously described. Non-limiting examples of suitable alkoxy groups include methoxy, ethoxy, n-propoxy and isopropoxy. The alkyl group is linked to an adjacent moiety through the ether oxygen.

"Alkylene" means an alkanediyl group commonly having free valencies on two carbon atoms. Non-limiting examples include methylene, ethylene, propylene and the like.

"Aryl" means an aromatic monocyclic or multicyclic ring system comprising about 6 to about 14 carbon atoms, preferably about 6 to about 10 carbon atoms. Included in the definition of aryl are fused aryls such as indenyl, napthalenyl, anthracenyl and indolinyl. Fused aryls can be attached to the parent moiety either through the saturated or unsaturated portions of the ring. The aryl group can be unsubstituted or substituted on the ring with one or more substituents which may be the same or different, each being independently selected from $R^4$ groups listed above. Non-limiting examples of suitable aryl groups include phenyl and naphthyl. The "aryl" group can also be substituted by linking two adjacent carbons on its aromatic ring via a combination of one or more carbon atoms and one or more oxygen atoms such as, for example, methylenedioxy, ethylenedioxy, and the like.

"Aralkyl" means an aryl-alkyl-group in which the aryl and alkyl are as previously described. Preferred aralkyls comprise a lower alkyl group. Non-limiting examples of suitable aralkyl groups include benzyl, 2-phenethyl and a naphthlenylmethyl. The bond to the parent moiety is through the alkyl. The term "substituted aralkyl" means that the aralkyl group may be substituted by one or more substituents which may be the same or different, each substituent being independently selected from $R^4$ groups listed above.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted on the ring by replacing an available hydrogen on the ring by one or more substituents which may be the same or different, each being independently selected from $R^{10}$ groups listed above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like.

"Halo" means fluoro, chloro, bromo or iodo groups. Preferred are fluoro, chloro or bromo, and more preferred are fluoro and chloro.

"Halogen" means fluorine, chlorine, bromine or iodine. Preferred are fluorine, chlorine or bromine, and more preferred are fluorine and chlorine.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted on the ring by replacing an available hydrogen on the ring by one or more substituents which may be the same or different, each being independently selected from $R^4$ groups listed above. A nitrogen atom of a heteroaryl can be optionally oxidized to the corresponding N-oxide. Non-limiting examples of suitable heteroaryls include pyridyl, pyrazinyl, furanyl, thienyl, pyrimidinyl, isoxazolyl, isothiazolyl, oxazolyl, thiazolyl, pyrrolyl, triazolyl, and the like.

"Heterocyclyl" means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. The heterocyclyl can be optionally substituted on the ring by replacing an available hydrogen on the ring or hydrogen(s) on any nitrogen(s) suitably by one or more substituents which may be the same or different, each being independently selected from $R^9$ group; listed above. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, pyranyl, thiophenyl, tetrahydrothiophenyl, morpholinyl and the like.

"Heterocyclylalkyl" means heterocyclyl-alkyl-group in which the heterocyclyl and alkyl are as previously described. The heterocyclyl ring can be optionally substituted on the ring by replacing an available hydrogen on the ring or hydrogen(s) on any nitrogen(s) suitably by one or more substituents which may be the same or different, each being independently selected from $R^9$ groups listed above. The nitrogen or sulfur atom of the heterocyclyl can be optionally oxidized to the corresponding N-oxide, S-oxide or S,S-dioxide. Non-limiting examples of suitable heterocyclylalkyl groups include

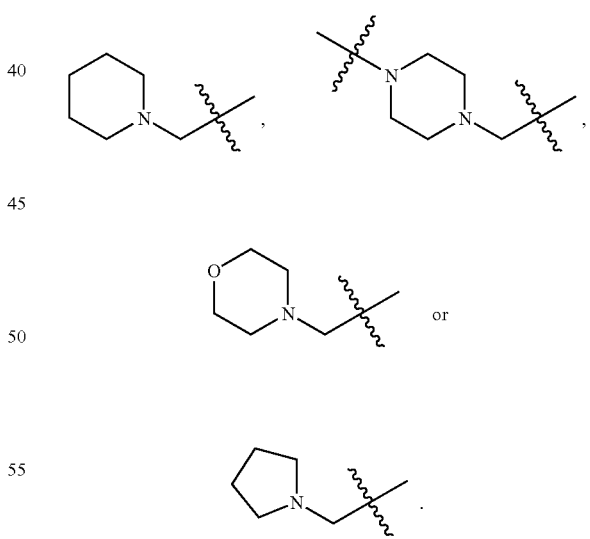

The bond to the parent moiety is through the alkyl.

"Hydroxyalkyl" means a HO-alkyl-group in which alkyl is as previously defined. Preferred hydroxyalkyls contain lower alkyl. Non-limiting examples of suitable hydroxyalkyl groups include hydroxymethyl and 2-hydroxyethyl.

"Mammal" means humans and other mammalian animals.

"Patient" includes both human and other animals.

It should also be noted that any heteroatom with unsatisfied valences in the text, schemes, examples, structural formulae, and Tables herein is assumed to have the hydrogen atom or atoms to satisfy the valences.

The terms "at least one "compound or "one or more compounds" means one to three compounds, preferably one compound.

When any variable (e.g., aryl, heterocycle, $R^2$, etc.) occurs more than once in any substituent or in Formula I, its definition at each occurrence is independent of its definition at every other occurrence. Also, combinations of substituents and/or variables are permissible only if such combinations result in stable compounds.

The compounds of Formula I can be administered as racemic mixtures or enantiomerically pure compounds within the scope of the present invention.

As used herein, the term "composition" is intended to encompass a product comprising the specified ingredients in the specified amounts, as well as any product which results, directly or indirectly, from combination of the specified ingredients in the specified amounts.

The compounds of formula I can form salts, solvates and prodrugs, which are also within the scope of this invention. Reference to a compound of formula I herein is understood to include reference to salts, solvates and prodrugs thereof, unless otherwise indicated.

Solvates of the compounds of the invention are also contemplated as within the scope of the present invention. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

Prodrugs of the compounds of the invention are also contemplated within the scope of this invention. The term "prodrug", as employed herein, denotes a compound that is a drug precursor which, upon administration to a subject, undergoes chemical conversion by metabolic or chemical processes to yield a compound of formula I or a salt and/or solvate thereof. A discussion of prodrugs is provided in T. Higuchi and V. Stella, *Pro-drugs as Novel Delivery Systems* (1987) Volume 14 of the A.C.S. Symposium Series, and in *Bioreversible Carriers in Drug Design*, (1987) Edward B. Roche, ed., American Pharmaceutical Association and Pergamon Press, both of which are incorporated herein by reference thereto.

The term "salt(s)", as employed herein, denotes acidic salts formed with inorganic and/or organic acids, as well as basic salts formed with inorganic and/or organic bases. In addition, when a compound of Formula I contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compound of the Formula I may be formed, for example, by reacting a compound of Formula I with an amount of acid or base, such as an equivalent amount, in a medium such as one in which the salt precipitates or in an aqueous medium followed by lyophilization.

Exemplary acid addition salts include acetates, adipates, alginates, ascorbates, aspartates, benzoates, benzenesulforiates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, 2-naphthalenesulfonates, nicotinates, nitrates, oxalates, pectinates, persulfates, 3-phenylpropionates, phosphates, picrates, pivalates, propionates, salicylates, succinates, sulfates, sulfonates (such as those mentioned herein), tartarates, thiocyanates, toluenesulfonates (also known as tosylates,) undecanoates, and the like. Additionally, acids which are generally considered suitable for the formation of pharmaceutically useful salts from basic pharmaceutical compounds are discussed, for example, by S. Berge et al, *Journal of Pharmaceutical Sciences* (1977) 66(1) 1–19; P. Gould, *International J. of Pharmaceutics* (1986) 33 201–217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glucamides, t-butyl amines, and salts with amino acids such as arginine, lysine and the like. Basic nitrogen-containing groups may be quarternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Compounds of Formula I, and salts and solvates thereof, may exist in their tautomeric form (for example, as an amide or imino ether). All such tautomeric forms are contemplated herein as part of the present invention.

All stereoisomers (for example, geometric isomers, optical isomers and the like) of the present compounds (including those of the salts and solvates of the compounds), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate" and the like, is intended to equally apply to the salt and solvate of enantiomers, stereoisomers, rotamers, tautomers or racemates of the inventive compounds.

Compounds of Formula I can be highly selective, high affinity Melanin Concentrating Hormone (MCH) receptor antagonists useful for the treatment of obesity.

An aspect of this invention is a method of treating a mammal (e.g., human) having a disease or condition mediated by MCH by administering a therapeutically effective amount of at least one compound of Formula I, or a pharmaceutically acceptable salt or solvate of said compound to the mammal.

"Effective amount" or "therapeutically effective amount" is meant to describe an amount of compound of the present invention effective to treat a mammal (e.g., human) having a disease or condition mediated by MCH, and thus producing the desired therapeutic effect (the treatment of obesity, obesity related disorders, metabolic and eating disorders).

A preferred dosage is about 0.001 to 100 mg/kg of body weight/day of the compound of Formula I. An especially preferred dosage is about 0.01 to 30 mg/kg of body weight/day of a compound of Formula I, or a pharmaceutically acceptable salt or solvate of said compound.

Still yet another aspect of this invention is a method of treating obesity comprising administering to a mammal in need of such treatment a therapeutically effective amount of at least one compound of Formula I, or a pharmaceutically acceptable salt or solvate of said compound.

A further aspect of this invention is a method for treating eating and metabolic disorders such as bulimia and anorexia comprising administering to a mammal a therapeutically effective amount of at least one compound of Formula I, or a pharmaceutically acceptable salt or solvate of said compound.

Another aspect of this invention is a method for treating hyperlipidemia comprising administering to a mammal a therapeutically effective amount of at least one compound of Formula I or a pharmaceutically acceptable salt or solvate of said compound.

Another aspect of this invention is a method for treating cellulite and fat accumulation comprising administering to a mammal a therapeutically effective amount of at least one compound of Formula I, or a pharmaceutically acceptable salt or solvate of said compound.

Another aspect of this invention is directed to a method for treating type II diabetes comprising administering to a mammal a therapeutically effective amount of at least one compound of Formula I or a pharmaceutically acceptable salt or solvate of said compound.

In addition to the "direct" effect of the compounds of this invention on the MCH subtype, there are diseases and conditions that can benefit from the weight loss such as, for example, insulin resistance, impaired glucose tolerance, Type II Diabetes, hypertension, hyperlipidemia, cardiovascular disease, gall stones, certain cancers, and sleep apnea.

This invention is also directed to pharmaceutical compositions, which comprise at least one compound of Formula I, or a pharmaceutically acceptable salt or solvate of said compound and at least one pharmaceutically acceptable carrier.

This invention is also directed to pharmaceutical compositions for the treatment of obesity which comprise an obesity treating amount of at least one compound of Formula I, or a pharmaceutically acceptable salt or solvate of said compound and at least one pharmaceutically acceptable carrier.

Still yet other aspects of this invention are combinations of a compound of Formula I, or a pharmaceutically acceptable salt or solvate of said compound and other compounds as described below.

Accordingly, included within the invention is a method for treating obesity comprising administering to a mammal (e.g., a female or male human)
  a. an amount of a first compound, said first compound being a compound of Formula I, or a pharmaceutically acceptable salt or solvate of said compound; and
  b. an amount of a second compound, said second compound being an antiobesity and/or anorectic agent such as a $B_3$ agonist, a thyromimetic agent, an anoretic agent, or an NPY antagonist and/or optionally a pharmaceutically carrier, vehicle or diluent, wherein the amounts of the first and second compounds result in a therapeutic effect.

Another aspect of this invention is a kit comprising:
  a. an amount of a compound of Formula I, or a pharmaceutically acceptable salt or solvate of said compound and a pharmaceutically acceptable carrier, vehicle or diluent in a first unit dosage form;
  b. an amount of an antiobesity and/or anorectic agent such as a $B_3$ agonist, a thyromimetic agent, an anoretic agent, or an NPY antagonist and a pharmaceutically acceptable carrier, vehicle or diluent in a second unit dosage form; and
  c. means for containing said first and second dosage forms wherein the amounts of the first and second compounds result in a therapeutic effect.

Preferred antiobesity and/or anorectic agents (taken singly or in any combination thereof) in the above combination methods, combination compositions and combination kits are:
  phenylpropanolamine, ephedrine, pseudoephedrine, phentermine, a cholecystokinin-A (hereinafter referred to as CCK-A) agonist, a monoamine reuptake inhibitor (such as sibutramine), a sympathomimetic agent, a serotonergic agent (such as dexfenfluramine or fenfluramine), a dopamine agonist (such as bromocriptine), a melanocyte-stimulating hormone receptor agonist or mimetic, a melanocyte-stimulating hormone analog, a cannabinoid receptor antagonist, a melanin concentrating hormone antagonist, the OB protein (hereinafter referred to as "leptin"), a leptin analog, a leptin receptor agonist, a galanin antagonist or a GI lipase inhibitor or decreaser (such as orlistat). Other useful anorectic agents include bombesin agonists, dehydroepiandrosterone or analogs thereof, glucocorticoid receptor agonists and antagonists, orexin receptor antagonists, urocortin binding protein antagonists, agonists of the glucagon-like peptide-1 receptor such as Exendin and ciliary neurotrophic factors such as Axokine.

Another aspect of this invention is a method of treating diabetes comprising administering to a mammal (e.g., a female or male human)

a. an amount of a first compound, said first compound being a compound of Formula I, or a pharmaceutically acceptable salt or solvate of said compound; and b. an amount of a second compound, said second compound being an aldose reductase inhibitor, a glycogen phosphorylase inhibitor, a sorbitol dehydrogenase inhibitor, a protein tyrosine phosphatase 1B inhibitor, a dipeptidyl protease inhibitor, insulin (including orally bioavailable insulin preparations), an insulin mimetic, metformin, acarbose, a PPAR-gamma ligand such as troglitazone, rosaglitazone, pioglitazone or GW-1929, a sulfonylurea, glipazide, glyburide, or chlorpropamide wherein the amounts of the first and second compounds result in a therapeutic effect.

This invention is also directed to a pharmaceutical combination composition comprising: a therapeutically effective amount of a composition comprising a first compound, said first compound being a compound of Formula I, or a pharmaceutically acceptable salt or solvate of said compound;

a second compound, said second compound being an aldose reductase inhibitor, a glycogen phosphorylate inhibitor, a sorbitol dehydrogenase inhibitor, a protein tyrosine phosphatase 1B inhibitor, a dipeptidyl protease inhibitor, insulin (including orally bioavailable insulin preparations), an insulin mimetic, metformin, acarbose, a PPAR-gamma ligand such as troglitazone, rosaglitazone, pioglitazone, or GW-1929, a sulfonylurea, glipazide, glyburide, or chlorpropamide; and optionally a pharmaceutical carrier, vehicle or diluent.

Another aspect of this invention is a kit comprising:

a. an amount of a compound of Formula I, or a pharmaceutically acceptable salt or solvate of said compound and a pharmaceutically acceptable carrier, vehicle or diluent in a first unit dosage form;

b. an amount of an aldose reductase inhibitor, a glycogen phosphorylase inhibitor, a sorbitol dehydrogenase inhibitor, a protein tyrosine phosphatase 1B inhibitor, a dipeptidyl protease inhibitor, insulin (including orally bioavailable insulin preparations), an insulin mimetic, metformin, acarbose, a PPAR-gamma ligand such as troglitazone, rosaglitazone, pioglitazone, or GW-1929, a sulfonylurea, glipazide, glyburide, or chlorpropamide and a pharmaceutically acceptable carrier, vehicle or diluent in a second unit dosage form; and c. means for containing said first and second dosage forms wherein the amounts of the first and second compounds result in a therapeutic effect.

Preferably, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 1 mg to about 1000 mg, preferably from about 1 mg to about 50 mg, more preferably from about 1 mg to about 25 mg, according to the particular application.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 1 mg/day to about 300 mg/day, preferably 1 mg/day to 50 mg/day, in two to four divided doses.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 70 percent active ingredient. Suitable solid carriers are known in the art, e.g. magnesium carbonate, magnesium stearate, talc, sugar, lactose. Tablets, powders, cachets and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Liquid form preparations include solutions, suspensions and emulsions. As an example may be mentioned water or water-propylene glycol solutions for parenteral injection.

Liquid form preparations may also include solutions for intranasal administration.

Aerosol preparations suitable for inhalation may include solutions and solids in powder form, which may be in combination with a pharmaceutically acceptable carrier, such as an inert compressed gas.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in unit dosage form. In such form, the preparation is subdivided into unit doses containing appropriate quantities of the active component, e.g., an effective amount to achieve the desired purpose.

Compounds of Formula I can be produced by processes known to those skilled in the art using either solution phase or solid phase synthesis as shown in the following reaction schemes, in the preparations and examples below.

Synthesis

The invention disclosed herein is exemplified by the following preparations and examples which should not be construed to limit the scope of the invention which is defined in the appended claims. Alternative mechanistic pathways and analogous structures will be apparent to those skilled in the art.

Where NMR data are presented, $^1$H spectra were obtained on either a Varian VXR-200 (200 MHz, $^1$H), Varian Gemini-300 (300 MHz) or XL-400 (400 MHz) and are reported as ppm down field from Me$_4$Si with number of protons, multiplicities, and coupling constants in Hertz indicated parenthetically. Where LC/MS data are presented, analyses was performed using an Applied Biosystems API-100 mass spectrometer and Shimadzu SCL-10A LC column: Altech platinum C18, 3 micron, 33 mm×7 mm ID; gradient flow: 0 min—10% CH$_3$CN, 5 min—95% CH$_3$CN, 7 min—95% CH$_3$CN, 7.5 min—10% CH$_3$CN, 9 min—stop. The observed parent ion using electro spray ionization are given.

The following abbreviations are utilized throughout the experimental procedures described below:

AcOEt or EtOAc means ethyl acetate;
EtONa means sodium ethoxide;
Bn means benzyl;
THF means tetrahydrofuran;
Boc means Butoxycarbonyl;
TFA means trifluoroacetic acid;
DIC means diisopropylcarbodiimide;
Dppf means diphenylphosphinoferrocene;
DCM means dichloromethane;
DIBAL means disobutyl aluminum hydride;
DMF means N,N-dimethylformamide;
NMR means nuclear magnetic resonance spectroscopy;
LC/MS means liquid chromatography mass spectrometry;
MS means mass spectrometry;
TLC means Thin layer chromatography;
Pd$_2$(dba)$_3$ means palladium dibenzylamino;
Ti(iOPr)$_4$ means titanium isopropoxide;
room temperature or rt (ambient) means about 25° C.;
NaBH(OAc$_3$) means sodium triacetoxyborohydride.

EXAMPLES

The following scheme illustrates a method for preparing the herein disclosed compounds:

General Synthetic Scheme:

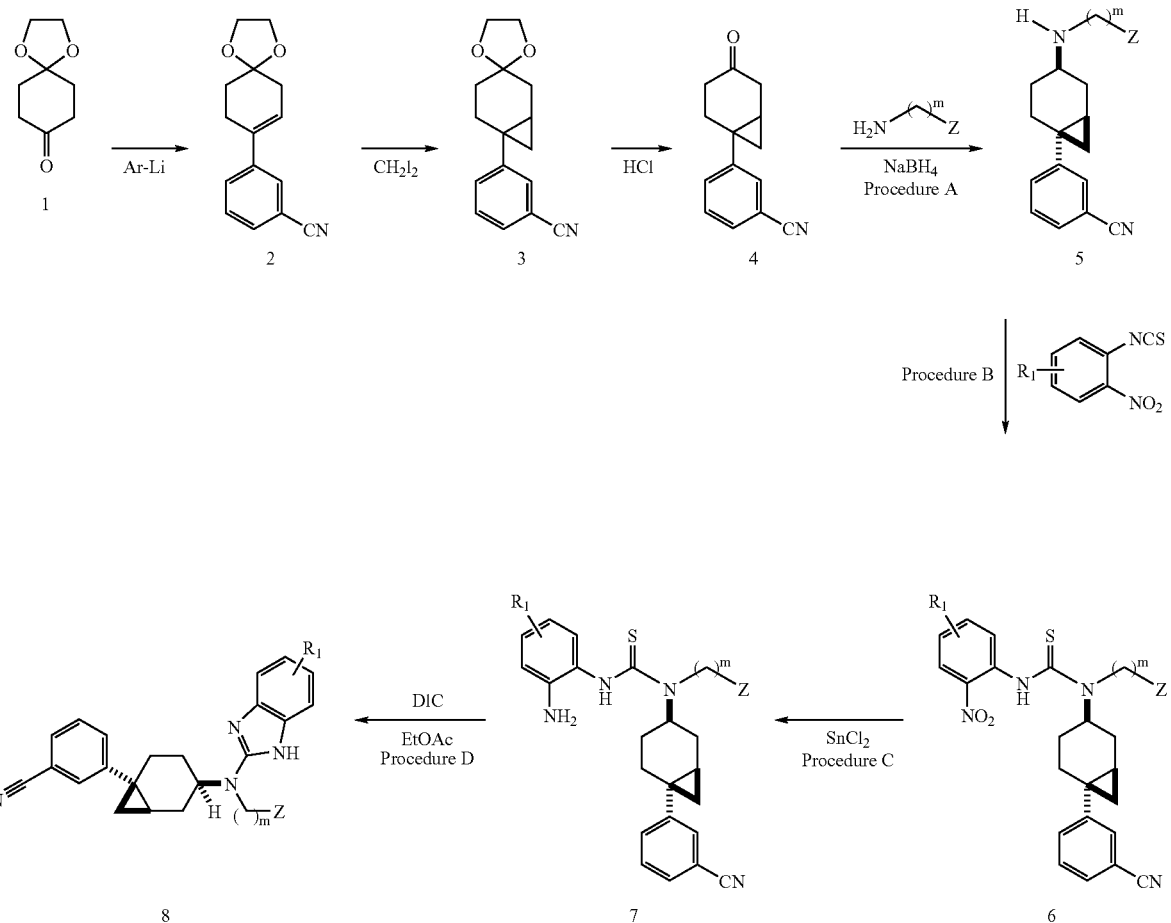

Synthetic schemes for substituted analogs are shown in greater detail in the experimental section below.

Experimental Procedures:

Note: These compounds can be prepared via the following schemes:

Scheme 1:
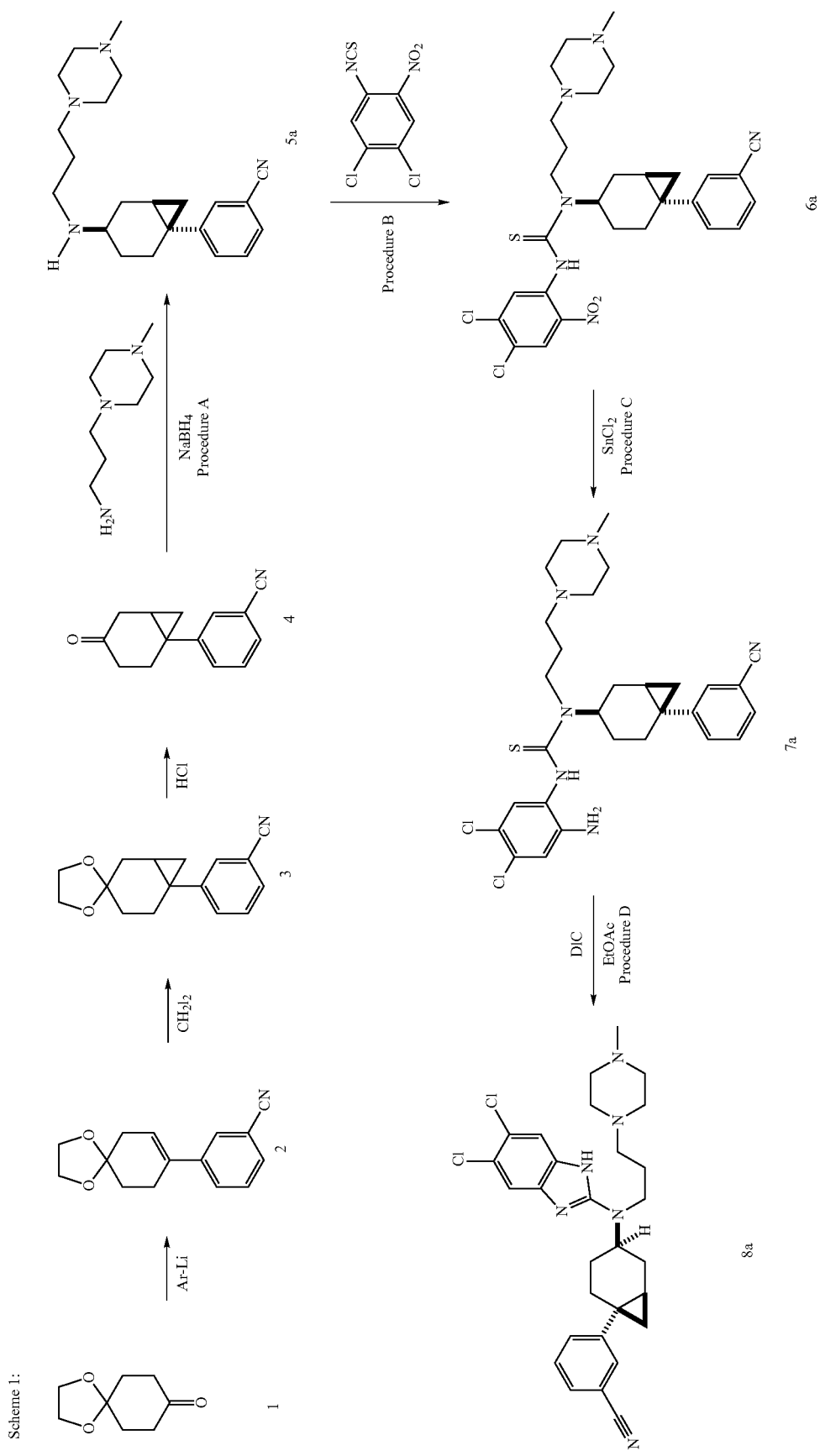

Compound 4 was made according to the procedure as shown in Scheme 1.

Procedure A:

Compound 5a: To a solution of 2.0 g (9.46 mmol) of compound 4 and 1.5 g (9.5 mmol) of 3-(4-methyl-piperazin-1-yl)-propylamine in 100 mL of dichloromethane (DCM) was added 2.8 mL (9.46 mmol) of titanium isopropoxide at 0° C. and the reaction was warmed to room temperature over 30 minutes. The reaction mixture was stirred at room temperature for 6 hours and 20 mL of methanol was added followed by 0.5 g of sodium borohydride (13.2 mmol). The reaction mixture was stirred overnight at room temperature and quenched by the addition of water. The reaction mixture was extracted with dichloromethane and the solvent was removed in vacuo. The product was isolated by silica gel column chromatography eluting with 30–50% methanol in dichloromethane to afford 3.0 g of product 5a as brown oil. Calcd m/z for $C_{22}H_{32}N_4H^+$=353.3; found m/z=353.1.

Procedure B:

Compound 6a: To a solution of 0.5 g (1.47 mmol) of compound 5a in 50 mL of dichloromethane was added 0.4 g (1.6 mmol) of 1,2-dichloro-4-isothiocyanato-5-nitro-benzene and the reaction was stirred overnight at room temperature. The reaction mixture was washed with water and dried over sodium sulfate. The solvent was removed in vacuo and the product was isolated by silica gel column chromatography eluting with 0–10% methanol in dichloromethane to afford 0.7 of compound 6a as yellow solid. Calcd m/z for $C_{29}H_{34}Cl_2N_6O_2S$ $H^+$=601.2; found m/z=601.1.

Procedure C:

Compound 7a: To a solution of 0.66g (1.09 mmol) of compound 6a in 20 mL of ethyl acetate was added 0.56 g (2 eq) of $SnCl_2.2H_2O$ and the contents were stirred at room temperature for 3 hours. The reaction mixture was diluted with 100 mL of ethyl acetate and passed through celite. The solvent was removed in vacuo to get 0.5 g of compound 7a as brown oil. It was used as such for the next step without purification. Calcd m/z for $C_{29}H_{36}Cl_2N_6S$ $H^+$=571.2; found m/z=571.1.

Procedure D:

Compound 8a: To a solution of 0.5 g (0.674 mmol) of compound 7a in 20 mL of ethyl acetate was added 0.255 g (3eq) of diisopropylcarbodiimide and the reaction was stirred at room temperature overnight. The reaction mixture was diluted with 100 mL of ethyl acetate and passed through a small pad of celite. The solvent was removed in vacuo and the product was isolated by silica gel column chromatography eluting with 0–10% methanol in dichloromethane to afford 0.285 g of compound 8a as off-white solid. Calcd m/z and found m/z for $C_{29}H_{34}Cl_2N_6H^+$, see table below.

The following compounds can be prepared analogously:

| Ex. | Structure and Example # | Mol. Formula | Mol. Wt. | Observed m/z |
|---|---|---|---|---|
| 8a | 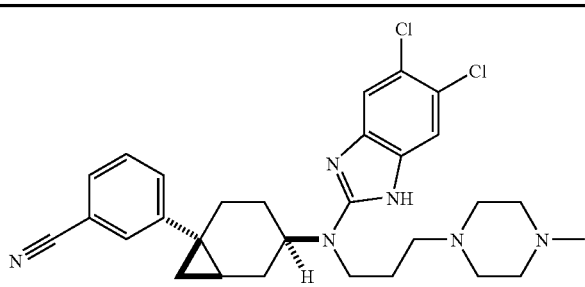 | $C_{29}H_{34}Cl_2N_6$ | 537.5 | 537.1 |
| 8b | 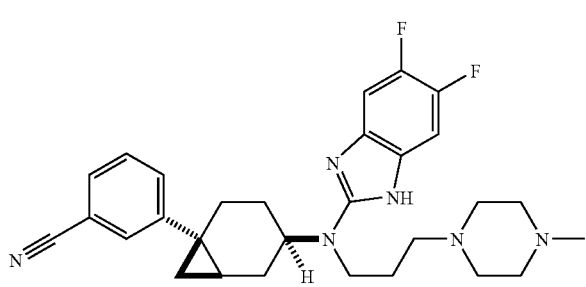 | $C_{29}H_{34}F_2N_6$ | 504.6 | 505.1 |
| 8c | 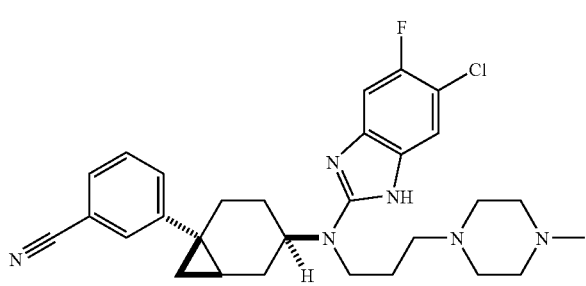 | $C_{29}H_{34}ClFN_6$ | 521.1 | 521.1 |

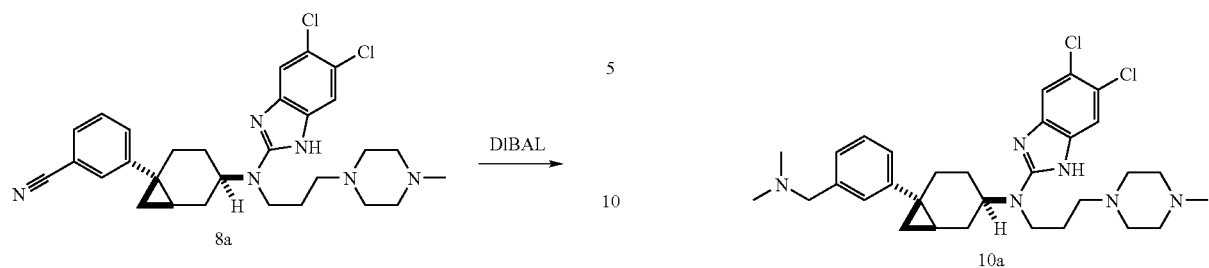

Compound 9a: To a solution of 0.2 g (0.572 mmol) of compound 8a in 10 mL of dichloromethane at −78° C. was added 1 mL (2 eq) of a solution of DIBAL (1.5 M in toluene), and the reaction was stirred for one hour. The reaction mixture was warmed to room temperature and stirred overnight. The reaction mixture was quenched by the addition of sodium sulfate decahydrate and stirred for 2 hours at room temperature. The reaction mixture was extracted with dichloromethane and the solvent was removed in vacuo. The product was isolated by silica gel column chromatography eluting with 10% methanol in dichloromethane to afford 0.12 g of aldehyde 9a as oil. Calcd m/z and found m/z for $C_{29}H_{35}Cl_2N_5$ $OH^+$, see table below.

The following compound was also prepared analogously:

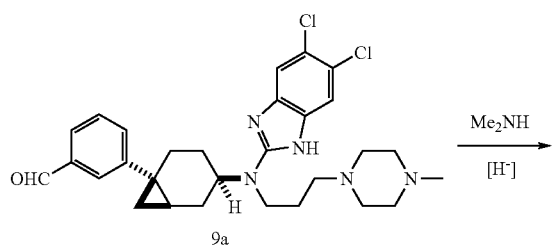

| Ex. | Structure and Example # | Mol. Formula | Mol. Wt. | Observed m/z |
|---|---|---|---|---|
| 9a | | $C_{29}H_{35}Cl_2N_5O$ | 540.5 | 540.1 |
| 9b | | $C_{29}H_{35}F_2N_5O$ | 507.6 | 508.1 |

Compound 10a: To a solution of 0.05 g (0.0925 mmol) of compound 9a in 10 mL of methanol was added dimethylamine hydrochloride (0.02 g, excess) followed by 0.032 g (0.15 mmol) of triacetoxysodium borohydride at room temperature and the mixture was stirred for 12 hours. The solvent was removed in vacuo and the product was isolated by preparative TLC eluting with 10% methanol in dichloromethane to afford 0.017 g of compound 10a as oil. Calcd m/z and found m/z for $C_{31}H_{42}Cl_2N_6H^+$, see table below.

The following compounds were prepared analogously:

| Ex. | Structure and Example # | Mol. Formula | Mol. Wt. | Observed m/z |
|-----|------------------------|--------------|----------|--------------|
| 10a | | $C_{31}H_{42}Cl_2N_6$ | 569.6 | 569.1 |
| 10b | | $C_{33}H_{44}Cl_2N_6O$ | 611.7 | 611.1 |
| 10c | | $C_{33}H_{44}F_2N_6$ | 562.7 | 563.1 |
| 10d | | $C_{31}H_{42}F_2N_6$ | 536.7 | 537.1 |

-continued

| Ex. | Structure and Example # | Mol. Formula | Mol. Wt. | Observed m/z |
|---|---|---|---|---|
| 10e | | $C_{33}H_{44}F_2N_6O$ | 578.7 | 579.1 |
| 10f | | $C_{33}H_{44}F_2N_6O$ | 578.7 | 579.1 |
| 10g | | $C_{34}H_{47}F_2N_7$ | 591.8 | 592.1 |
| 10h | | $C_{34}H_{46}F_2N_6$ | 576.8 | 577.1 |

| Ex. | Structure and Example # | Mol. Formula | Mol. Wt. | Observed m/z |
|---|---|---|---|---|
| 10i | | $C_{34}H_{46}F_2N_6O$ | 592.8 | 593.1 |

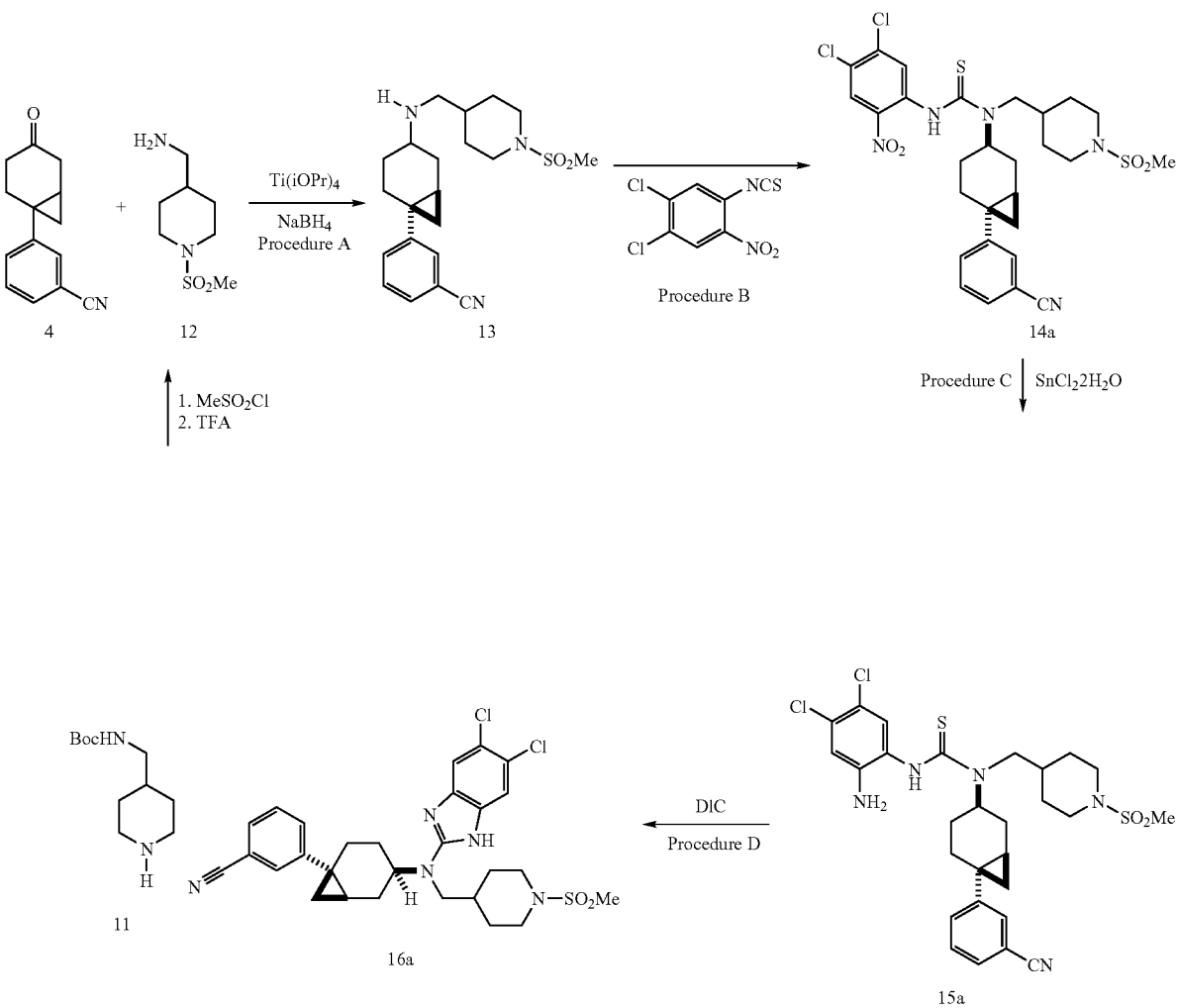

Scheme 3:

Compound 12: To a solution of 2.0 g (9.3 mmol) of compound 11 in 10 mL of dichloromethane was added 2.4 mL of Hunig's base (1.5 eq) followed by 3.5 mL of methanesulfonyl chloride (excess) at 0° C. The reaction mixture was warmed to room temperature and stirred overnight. The mixture was passed through a small pad of silica gel and the solvent was removed in vacuo to give ~1 g of residue which was deprotected using 2 mL of trifluoroacetic acid in 4 mL of dichloromethane to afford 1.36 g of compound 12 as its TFA salt. Calcd m/z for $C_7H_{16}N_5O_2S$ $H^+$=193.1; found m/z=193.1.

Compound 13: Reductive amination of compound 4 (0.88 g, 4.2 mmol) with compound 12 (0.8 g, 4.2 mmol) according to procedure A afforded 0.9 g of compound 13 as oil. Calcd m/z for $C_{21}H_{29}N_3O_2S$ $H^+$=388.2; found m/z=388.4.

Compound 14a: Compound 13 (0.2 g, 0.52 mmol) was treated with 1,2-dichloro-4-isothiocyanato-5-nitro-benzene (0.3 g, excess) according to procedure B to give 0.18 g of compound 14a as yellow solid. Calcd m/z for $C_{28}H_{31}Cl_2N_5O_4S_2H^+$=636.1; found m/z=636.1.

Compound 15a: Compound 14a (0.15 g, 0.52 mmol) was reduced according to procedure C to get 0.1 g of compound 15a as oil. Calcd m/z for $C_{28}H_{33}Cl_2N_5O_2S_2H^+$=605.1; found m/z=606.1.

Compound 16a: Compound 15a (0.1 g, 0.16 mmol) was cyclized according to procedure D to afford 0.011 g of compound 16a as pale brown solid. Calcd m/z and found m/z for $C_{28}H_{31}Cl_2N_5O_2S$ $H^+$, see table below.

The following compounds were prepared analogously:

| Ex. | Structure and Example # | Mol. Formula | Mol. Wt. | Observed m/z |
|---|---|---|---|---|
| 16a | 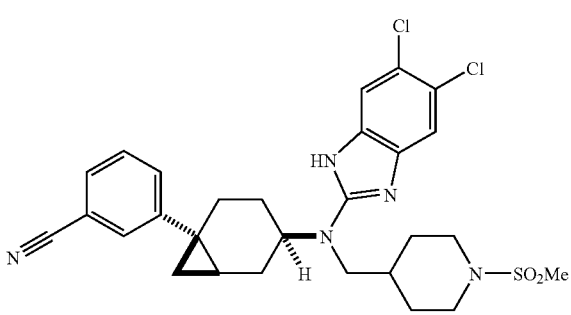 | $C_{28}H_{31}F_2N_5O_2S$ | 572.6 | 572.1 |
| 16b | 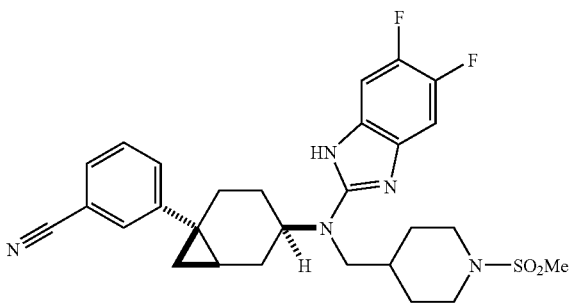 | $C_{28}H_{31}F_2N_5O_2S$ | 539.6 | 540.1 |
| 16c | 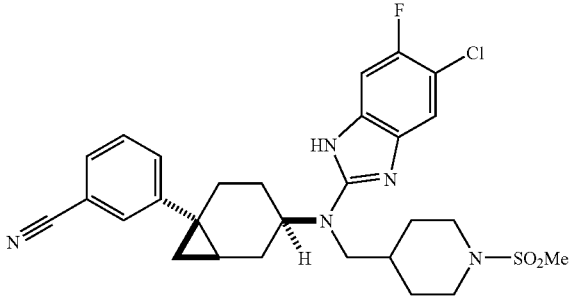 | $C_{28}H_{31}ClFN_5O_2S$ | 556.1 | 556.3 |

Scheme 4:
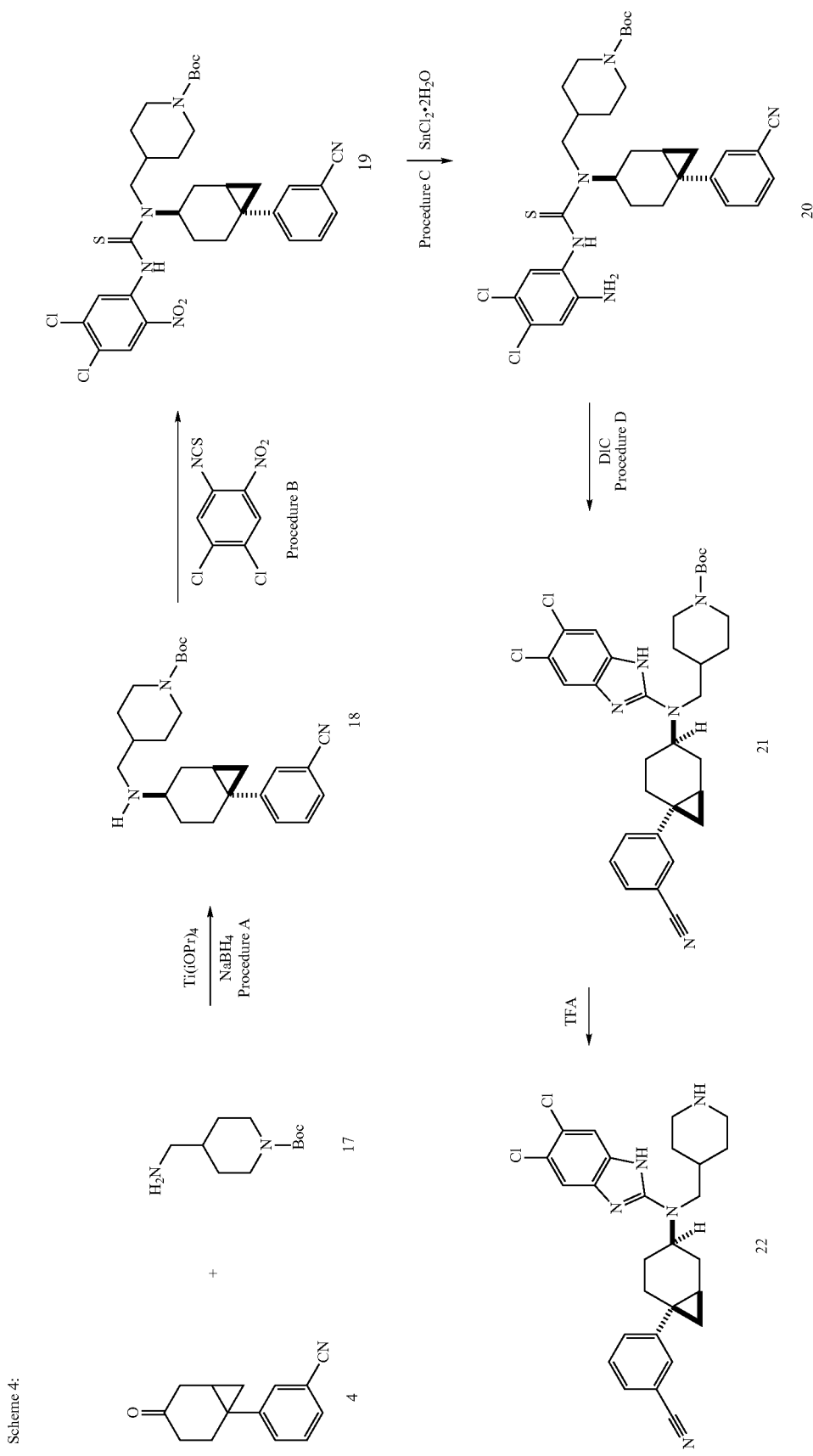

Compound 18: Reductive amination of compound 4 (2.2 g, 10.4 mmol) with compound 17 (2.0 g, 9.3 mmol) according to procedure A afforded 0.95 g of compound 18 as oil. Calcd m/z for $C_{25}H_{35}N_3O_2H^+$=410.3; found m/z=410.3.

Compound 19: Compound 18 (0.9 g, 2.19 mmol) was treated with 1,2-dichloro-4-isothiocyanato-5-nitro-benzene (0.9 g, excess) according to procedure B to get 1.15 g of compound 19 as yellow solid. Calcd m/z for $C_{32}H_{37}Cl_2N_5O_4S\ H^+$=658.2; found m/z=660.2.

Compound 20: Compound 19 (0.56 g, 0.85 mmol) was reduced according to procedure C to get 0.45 g of compound 20 as oil. Calcd m/z for $C_{32}H_{39}Cl_2N_5O_2S\ H^+$=628.2; found m/z=628.2.

Compound 21: Compound 20 (0.45 g, 0.71 mmol) was cyclized according to procedure D to afford 0.29 g of compound 21 as off-white solid. Calcd m/z for $C_{32}H_{37}Cl_2N_5O_2H^+$=594.2; found m/z=594.1.

Compound 22: Compound 21 (0.027 g, 0.45 mmol) was treated with trifluoroacetic acid (1 mL) in 5 mL of dichloromethane at 0° C. and stirred for 30 minutes. The solvent was removed in vacuo and the product was isolated by silica gel column eluting with 0–10% methanol in dichloromethane to afford 0.1 g of compound 22 as oil. Calcd m/z for $C_{27}H_{29}Cl_2N_5H^+$=494.2; found m/z=494.1.

Scheme 5:

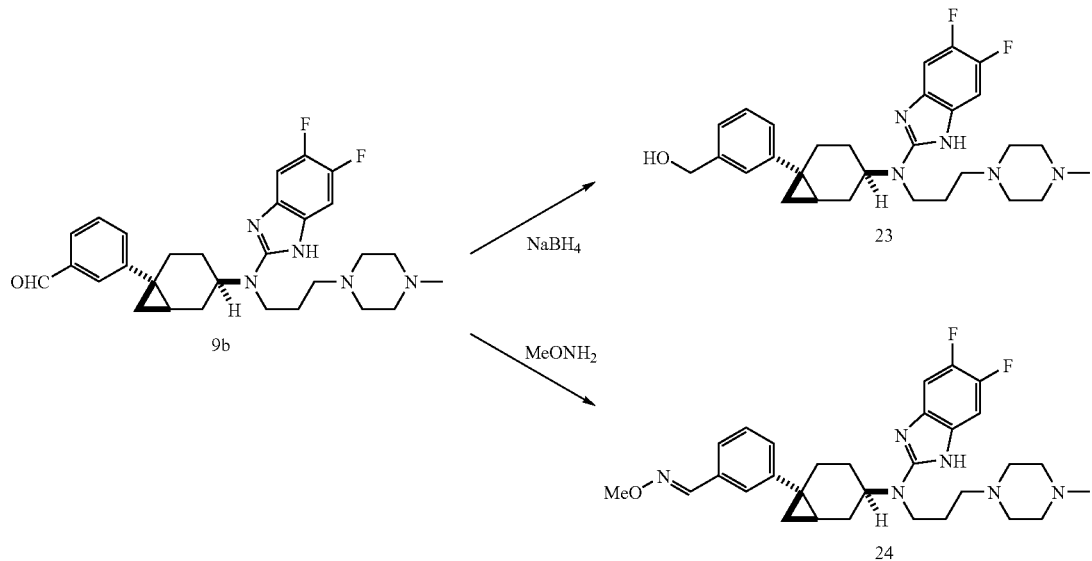

Compound 23: To a solution of 10 mg (0.019 mmol) of compound 9b in 1 mL of methanol was added 5 mg (0.13 mmol) of NaBH$_4$ at room temperature and the reaction was stirred for 10 minutes. Water (2 drops) was added and the solvent was removed in vacuo. The product was isolated by prep TLC eluting with 10% methanol in dichloromethane to afford 4 mg of compound 23 as oil. Calcd m/z for $C_{29}H_{37}F_2N_5O\ H^+$=510.3; found m/z=510.1.

Compound 24: To a solution of 10 mg (0.019 mmol) of compound 9b in 1 mL of methanol was added 2 drops of pyridine followed by methoxylamine hydrochloride (10 mg, excess) at room temperature. The reaction mixture was stirred at room temperature for 2 hours and the solvent was removed in vacuo. The product was isolated by prep TLC eluting with 10% methanol in dichloromethane to afford 3 mg of compound 24 as oil. Calcd m/z for $C_{30}H_{38}F_2N_6O\ H^+$=537.3; found m/z=537.1.

Scheme 6:
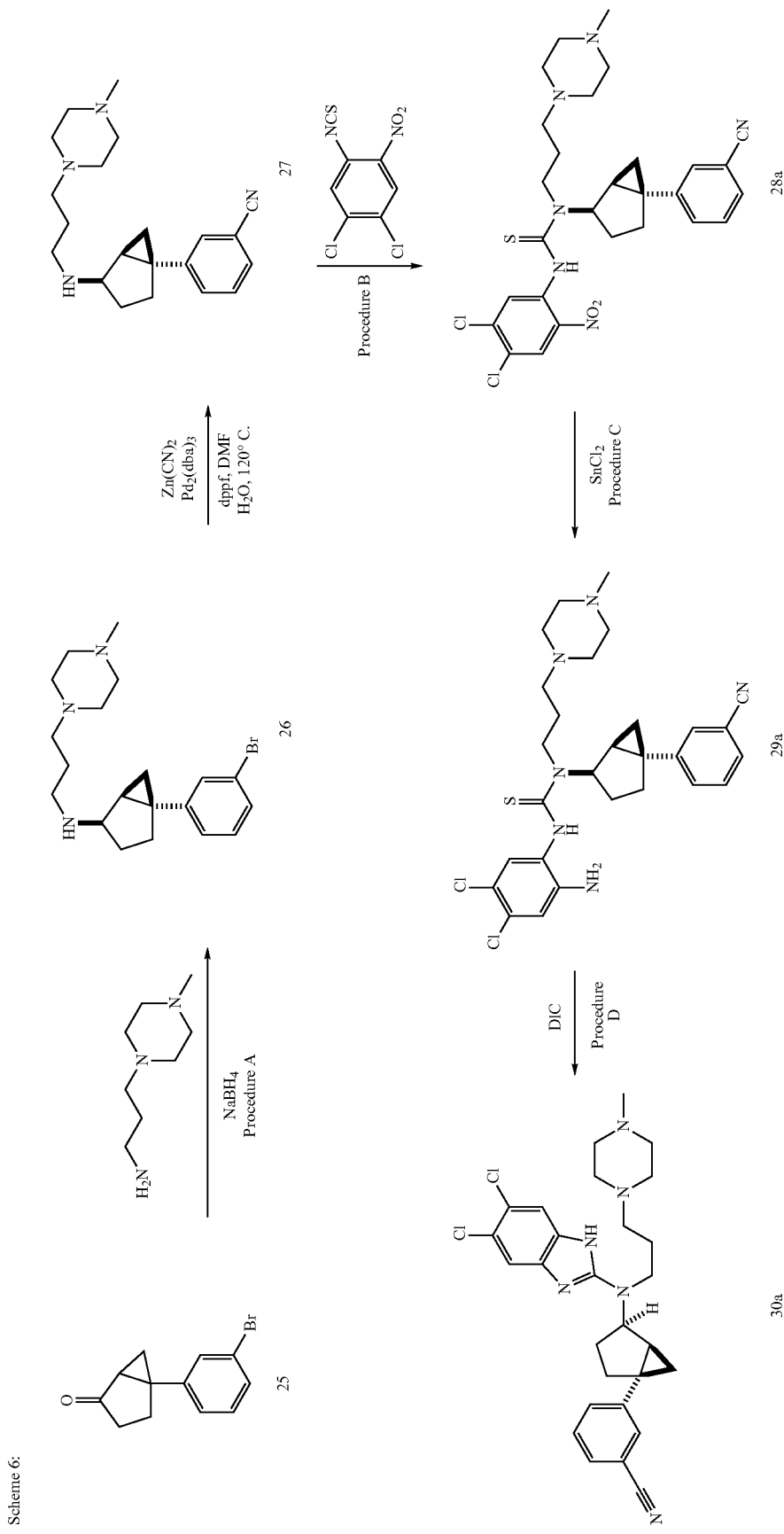

Compound 26: Reductive amination of compound 25 (0.78 g, 3.7 mmol) with 3-(4methyl-piperazin-1-yl)-propylamine (0.68 g, 7.3 mmol) according to procedure A afforded 0.5 g of compound 26 as oil. Calcd m/z for $C_{20}H_{30}BrN_3H^+$= 392.2; found m/z=392.1.

Compound 27: To a solution of 3.07 g (7.82 mmol) of compound 26 in dimethylformamide was added 0.95 g (8.0 mmol) of zinc cyanide followed by dppf (0.525 g, 12 mol %) at room temperature. Water (200 µL) was added followed by $Pd_2(dba)_3$ and the solution was degassed with nitrogen for 5 minutes. The contents were heated at 120° C. for 3 hours. The reaction mixture was diluted with dichloromethane and washed with water. The solvent was removed in vacuo and the product was isolated by silica gel column chromatography eluting with 20% methanol in dichloromethane to afford 2.5 g of compound 27 as oil. Calcd m/z for $C_{21}H_{30}N_4H^+$= 339.3; found m/z=339.3.

Compound 28a: Compound 27 (0.8 g, 2.36 mmol) was treated with 1,2-dichloro-4-isothiocyanato-5-nitro-benzene (0.65 g, 2.6 mmol) according to procedure B to get 1.0 g of compound 28a as yellow solid. Calcd m/z for $C_{28}H_{32}Cl_2N_6O_2H^+$=587.2; found m/z=587.1.

Compound 29a: Compound 28a (1.0 g, 1.7 mmol) was reduced according to procedure C to get 0.5 g of compound 29a as oil. Calcd m/z for $C_{28}H_{34}Cl_2N_6S\ H^+$=557.2; found m/z=557.2.

Compound 30a: Compound 29a (0.2 g, 0.358 mmol) was cyclized according to procedure D to afford 0.03 g of compound 30a as brown solid. Calcd m/z and found m/z for $C_{28}H_{32}Cl_2N_6H^+$, see table below.

The following compounds were prepared analogously:

| Ex. | Structure and Example # | Mol. Formula | Mol. Wt. | Observed m/z |
|---|---|---|---|---|
| 30a | | $C_{28}H_{32}Cl_2N_6$ | 523.5 | 523.1 |
| 30b | | $C_{28}H_{32}ClFN_6$ | 507.1 | 507.1 |
| 30c | | $C_{28}H_{32}F_2N_6$ | 490.6 | 491.1 |

Scheme 7:

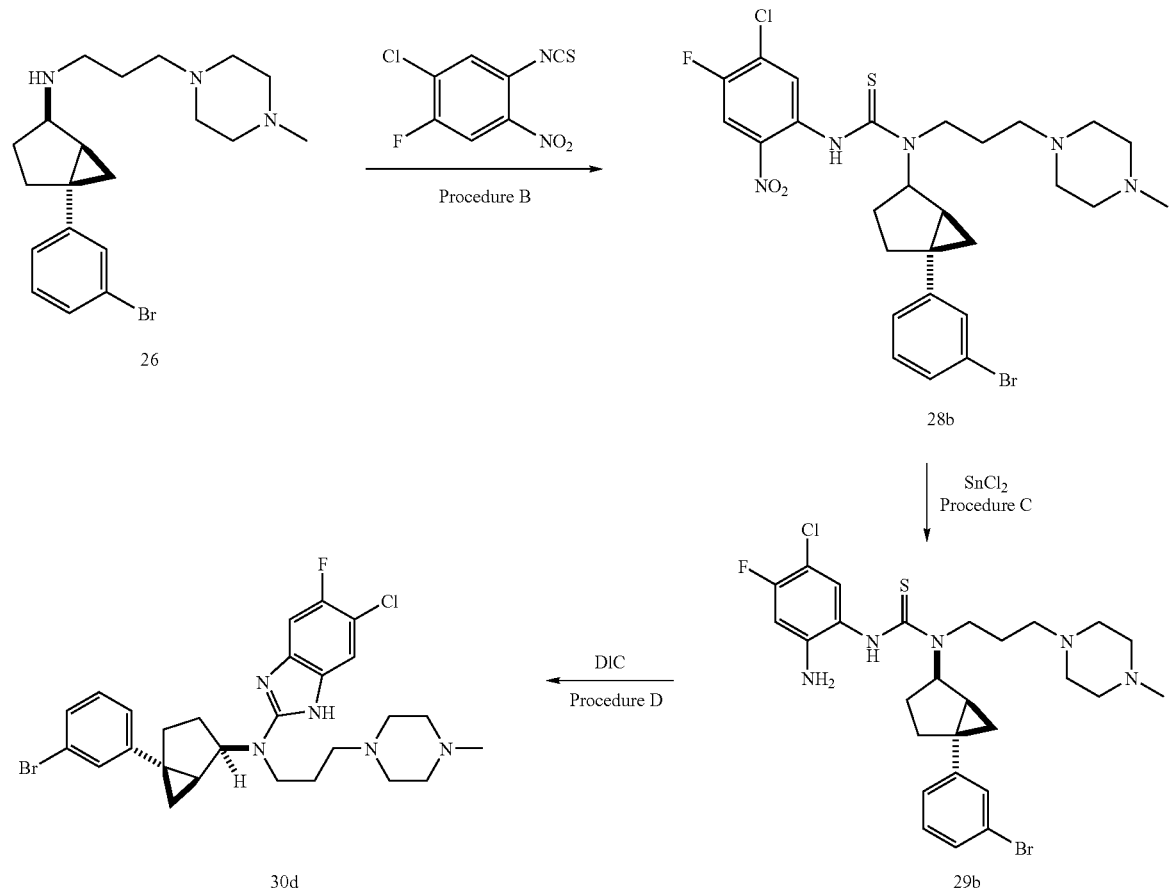

Compound 28b: Compound 26 (0.9 g, 2.29 mmol) was treated with 1-chloro-2-fluoro-5-isothiocyanato-4-nitrobenzene (0.6 g, 2.57 mmol) according to procedure B to get 0.75 g of compound 28b as yellow solid. Calcd m/z for $C_{27}H_{32}BrClFN_5O_2S$ $H^+$=624.12; found m/z=626.1.

Compound 29b: Compound 28b (0.5 g, 0.8 mmol) was reduced according to procedure C to get 0.25 g of compound 29b as off-white semisolid. Calcd m/z for $C_{27}H_{34}BrClFN_5O_2S$ $H^+$=594.15; found m/z=594.1.

Compound 30d: Compound 29b (0.1 g, 0.168 mmol) was cyclized according to procedure D to afford 0.03 g of compound 30d as off-white solid. Calcd m/z for $C_{27}H_{32}BrClFN_5H^+$=560.16; found m/z=562.1.

Scheme 8:

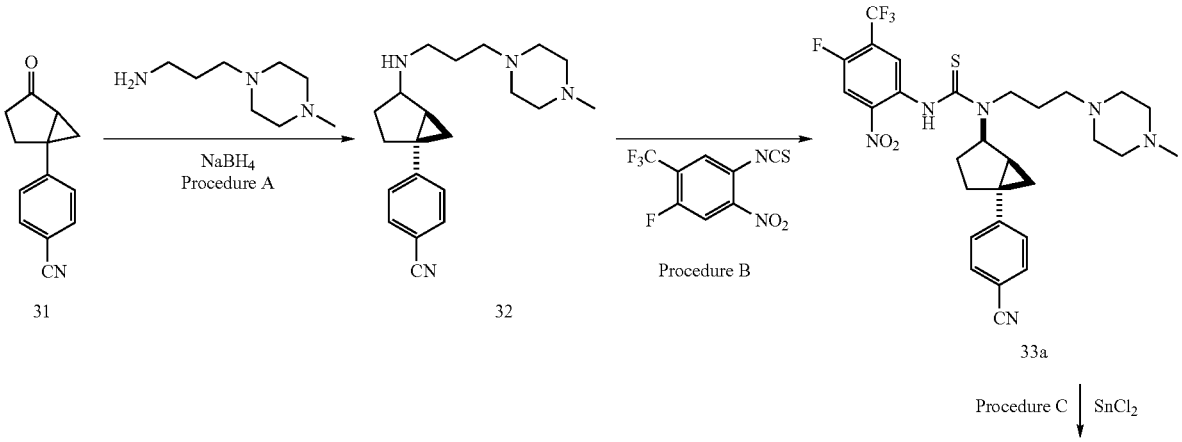

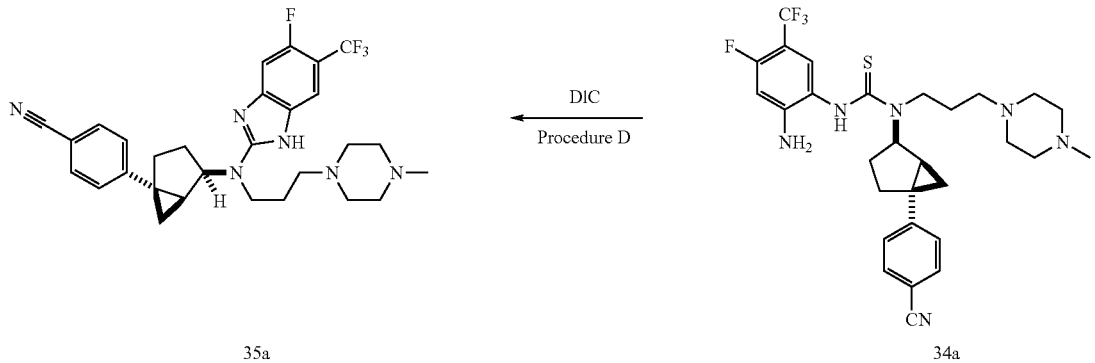

Compound 32: Reductive amination of 1.0 g (5 mmol) of compound 4 with 0.82 g (5.2 mmol) of 3-(4-methyl-piperazin-1-yl)-propylamine according to procedure A afforded 1.5 g of compound 32 as oil. Calcd m/z for $C_{21}H_{30}N_4H^+$= 339.3; found m/z=339.4.

Compound 33a: Compound 32 (0.4 g, 1.18 mmol) was treated with 0.35 g (1.5 mmol) of 1-fluoro-4-isothiocyanato-5-nitro-2-trifluoromethyl-benzene according to procedure B to get 0.5 g of compound 33a as yellow solid. Calcd m/z for $C_{29}H_{32}F_4N_6O_2S\ H^+$=605.2; found m/z=605.1.

Compound 34a: Compound 33a (0.25 g, 0.413 mmol) was reduced according to procedure C to get 0.2 g of compound 34a as oil. Calcd m/z for $C_{29}H_{34}F_4N_6H^+$=575.3; found m/z=575.1.

Compound 35a: Compound 34a (0.2 g, 0.548 mmol) was cyclized according to procedure D to afford 0.05 g of compound 35a as off-white solid. Calcd m/z for $C_{29}H_{32}F_4N_6H^+$=541.3; found m/z=541.1.

The following compounds were prepared analogously:

| Ex. | Structure and Example # | Mol. Formula | Mol. Wt. | Observed m/z |
|---|---|---|---|---|
| 35a | | $C_{29}H_{32}F_4N_6$ | 540.6 | 541.1 |
| 35b | | $C_{28}H_{32}Cl_2N_6$ | 523.5 | 523.1 |
| 35c | | $C_{28}H_{32}ClFN_6$ | 507.1 | 507.1 |

Scheme 9:

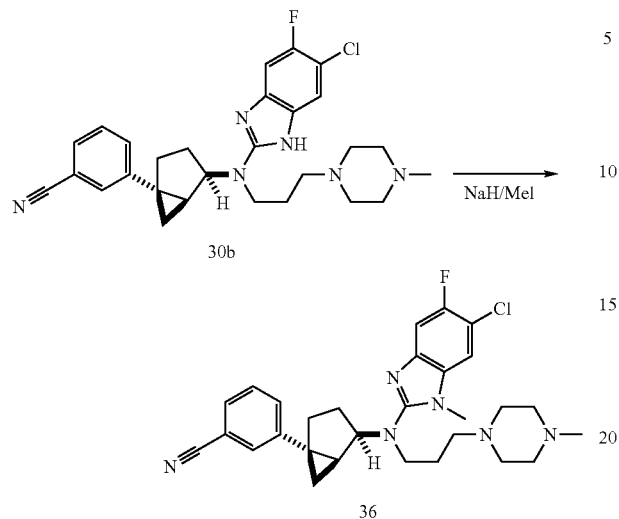

Compound 36: To a solution of 0.025 g (0.049 mmol) of compound 30b in tetrahydrofuran at 0° C. was added NaH (5 mg, excess) and the reaction was stirred for 10 minutes. The reaction mixture was warmed to room temperature and stirred for 15 minutes. MeI (0.01 g, 0.07 mmol) was added at 0° C. and the mixture was slowly warmed to room temperature and stirred for 3 hours. The reaction mixture was quenched by the addition of water and extracted with dichloromethane. The product was isolated by prep TLC eluting with 10% methanol in dichloromethane to afford 6 mg of compound 36 as oil. Calcd m/z for $C_{29}H_{34}ClFN_6H^+$ =521.2; found m/z=521.1.

MCH Receptor Binding Assay:

Membranes from CHO cells expressing the MCH receptor were prepared by lysing cells with 5 mM HEPES for 15 min at 4C. Cell lysates were centrifuged (12.5000×g, 15 min) and the pellet was resuspended in 5 mM HEPES. For each 96-well plate (Microlite, Dynex Technologies), 1 mg of cell membranes were incubated with 10 mg of wheat germ agglutinin SPA beads (Amersham) for 5 min at 4 C in a volume of 10 ml of binding buffer (25 mM HEPES, 10 mM $MGCl_2$, 10 mM NaCl, 5 mM $MnCl_2$, 0.1% BSA). The membrane/bead mixture was centrifuged (1500×g, 3.5 min), the supernatant was aspirated, and the pellet was resuspended in 10 ml binding buffer. The centrifugation, aspiration and resuspension were then repeated. The membrane/bead mixture (100 μl) was then added to 96-well plates containing 50 μl of 500 pM [$^{125}$I]-MCH (NEN) and 50 ml of the appropriate concentration of compound (4× the desired final concentration). Nonspecific binding was determined by including 1 μM MCH in the binding reaction. The binding reaction was incubated at room temperature for 2 h. Plates were then analyzed in a TOPCOUNT microplate scintillation counter (Packard). Data was analyzed and Ki values were determined using GraphPad Prism.

Compounds with Ki values greater than 100 nM are designated in the table below as D class compounds.

Compounds with Ki values between 30 and 100 nM are designated in the table below as C class compounds.

Compounds with Ki values between 10 and 30 nM are designated in the table below as B class compounds.

Compounds with Ki values less than 10 nM are designated in the table below as A class compounds.

In a preferred embodiment of the invention, Example 8a, a Ki value of 2.2 nM was observed.

| Ex. | Activity Class |
| --- | --- |
| 8a | A |
| 8b | A |
| 8c | A |
| 9a | B |
| 9b | B |
| 10a | A |
| 10b | B |
| 10c | B |
| 10d | D |
| 10e | B |
| 10f | D |
| 10g | D |
| 10h | D |
| 10i | D |
| 16a | A |
| 16b | B |
| 16c | A |
| 21 | D |
| 22 | A |
| 23 | C |
| 24 | B |
| 30a | A |
| 30b | A |
| 30c | B |
| 30d | B |
| 35a | A |
| 35b | B |
| 35c | A |
| 36 | D |

What is claimed:

1. A compound represented by the structural formula

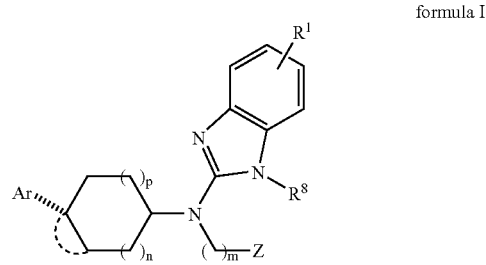

formula I or a pharmaceutically acceptable salt or solvate thereof, wherein
the dashed line in

represents either
(i) an optional bond which may be present or absent, and if present, forms a double bond with the single bond it is adjacent to, or
(ii) —C($R^5R^8$)—, —C($R^5R^8$)—C($R^5R^8$)— or —C($R^{11}R^{12}$)—;
m is 1, 2, 3 or 4;
n is 0, 1 or 2;

p is 0, 1 or 2;

Ar is aryl, heteroaryl, $R^4$-substituted aryl or $R^4$-substituted heteroaryl;

Z is —$NR^5R^6$, —$NR^5C(O)R^3$, —$C(O)NR^5R^6$, —$NR^5C(O)NR^5R^6$, —$NR^5C(O)OR^3$, —$NR^5S(O_2)R^3$, —$S(O_2)NR^5R^6$, —$S(O_2)R^3$, —$C(O)R^3$, —$C(O)OR^6$, —OH, alkoxy,

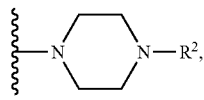

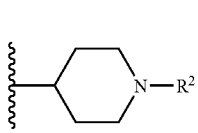 or 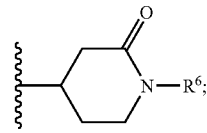;

$R^1$ is 1 to 4 moieties, each $R^1$ is independently selected from the group consisting of hydrogen, —OH, halogen, alkyl, alkoxy, —$OCF_3$, —$CF_3$ or —CN, or two $R^1$ moieties on adjacent carbons of the cycloalkyl ring can be joined together to form a methylenedioxy or ethylenedioxy group;

$R^2$ is hydrogen, alkyl, $R^{10}$-substituted alkyl, cycloalkyl, $R^{10}$-substituted cycloalkyl, aralkyl, heterocyclyl, —$C(O)R^3$, —$S(O_2)R^3$ or —$C(O)NR^5R^6$;

$R^3$ is alkyl, aryl, aralkyl, heteroaryl, $R^4$-substituted aralkyl, $R^4$-substituted aryl or $R^4$-substituted heteroaryl;

$R^4$ is 1 to 5 moieties, each $R^4$ is independently selected from the consisting of hydrogen, heterocyclyl, $R^9$-substituted heterocyclyl, heterocyclylalkyl-, $R^9$-substituted heterocyclylalkyl, —OH, -alkoxy, —$OCF_3$, —CN, alkyl, halogen, —$NR^5R^6$, —$NR^5C(O)R^7$, —$C(O)NR^5R^6$, —$NR^5S(O_2)R^7$, —$S(O_2)NR^5R^6$, —$S(O_2)R^7$, —$COR^7$, —$C(O)OR^5$, —$CF_3$, -(alkylene)$NR^5R^6$, -(alkylene)$NR^6C(O)R^7$, -(alkylene)$NR^6S(O_2)R^7$, -(alkylene), —$NR^5C(O)NR^5R^6$, -(alkylene)$NR^5C(O)OR^7$, CHO, —C=($NOR^5$) and

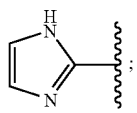

$R^5$ is hydrogen or alkyl;
$R^6$ is hydrogen, alkyl, aryl, aralkyl or heteroaryl;
$R^7$ is alkyl, aryl, aralkyl or heteroaryl;
$R^8$ is hydrogen or alkyl;
$R^9$ is alkyl, —OH or hydroxyalkyl;
$R^{10}$ is alkoxy, halogen, —$C(O)NR^5R^6$, —$C(O)OR^6$, —$NR^5R^6$ or —OH;
$R^{11}$ is hydrogen or halogen; and
$R^{12}$ is hydrogen or halogen.

2. The compound of claim 1 wherein the dashed line in

is —$CH_2$—.

3. The compound of claim 1 wherein m is 1 or 3.
4. The compound of claim 1 wherein n is 0 or 1.
5. The compound of claim 1 wherein p is 1.
6. The compound of claim 1 wherein Ar is $R^4$-substituted aryl or $R^4$-substituted heteroaryl.
7. The compound of claim 1 wherein Z is

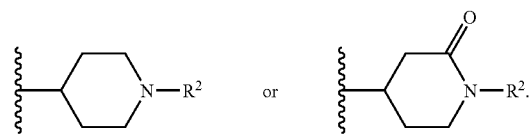

8. The compound of claim 1 wherein $R^1$ is substituted on the parent ring as follows

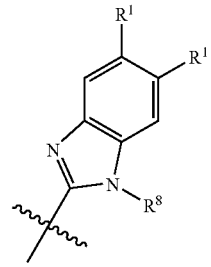

and $R^8$ is hydrogen or alkyl.

9. The compound of claim 1 wherein $R^2$ is hydrogen, Boc, alkyl or —$S(O_2)R^3$.
10. The compound of claim 1 wherein $R^3$ is alkyl.
11. The compound of claim 1 wherein $R^4$ is -(alkylene)$NR^5R^6$, —CN, alkoxy, $R^9$-substituted heterocyclyl, CHO, —C=($NOR^5$), heterocyclylalkyl-, $R^9$-substituted heterocyclylalkyl or halogen.
12. The compound of claim 1 wherein $R^9$ is alkyl, —OH or hydroxyalkyl.
13. The compound of claim 1 wherein
the dashed line in is

—$CH_2$—;
m is 1 or 3;
n is 0 or 1;
p is 1;
Ar is $R^4$-substituted aryl or $R^4$-substituted heteroaryl;

Z is

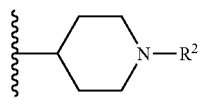 or 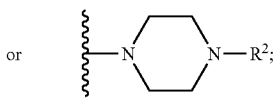

R¹ is substituted on the parent ring as follows

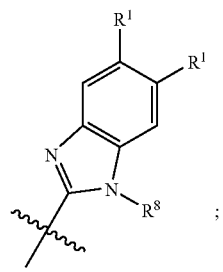

R² is hydrogen, Boc, alkyl or —S(O₂)R³;
R³ is alkyl;
R⁴ is -(alkylene)NR⁵R⁶, —CN, alkoxy, R⁹-substituted heterocyclyl, CHO, —C=(NOR⁵), heterocyclylalkyl-, R⁹-substituted heterocyclylalkyl or halogen;
R⁸ is hydrogen or alkyl; and
R⁹ is alkyl, —OH or hydroxyalkyl.

14. The compound of claim 13 wherein the R¹ moieties are halogen or CF₃.

15. The compound of claim 13 wherein R² is methyl.

16. The compound of claim 13 wherein R³ is methyl.

17. The compound of claim 13 wherein R⁴ is —CN, alkoxy, -(alkylene)NR⁵R⁶, R⁹-substituted heterocyclyl, —C=(NOR⁵), heterocyclylalkyl-, R⁹-substituted heterocyclylalkyl- or halogen.

18. The compound of claim 13 wherein R⁴ is —CN, —CH₂N(CH₃)₂, Br, —C=NOCH₃,

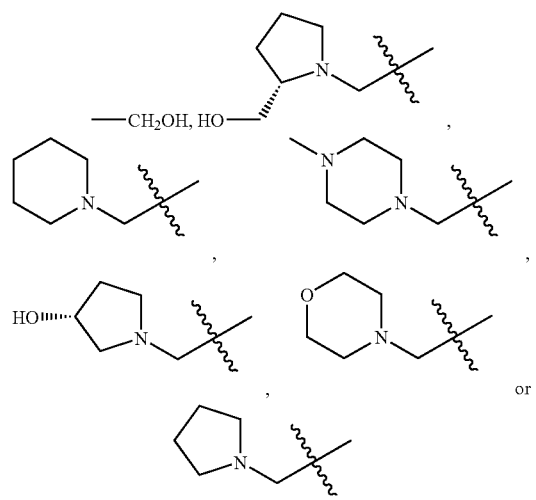

19. The compound of claim 13 wherein R⁸ is hydrogen or methyl.

20. The compound of claim 13 wherein Z is

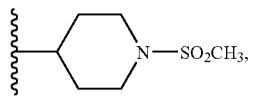 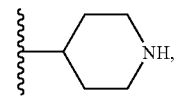

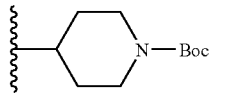 or 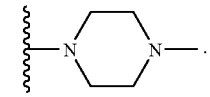

21. The compound of claim 1 wherein the dashed line in

is —CH₂—;
m is 3;
n is 1;
p is 1;
Ar is R⁴-substituted aryl or R⁴-substituted heteroaryl;
Z is

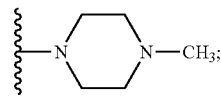

R¹ is halogen where said R¹ is substituted on the parent ring as follows

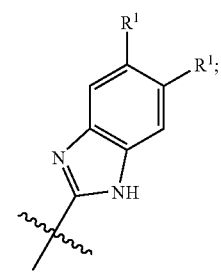

and
R⁴ is —CN, alkoxy, -(alkylene)NR⁵R⁶, R⁹-substituted heterocyclyl, —C=(NOR⁵), heterocyclylalkyl-, R⁹-substituted heterocyclylalkyl- or halogen.

22. The compound of claim 1 wherein the dashed line in

is —CH₂—;
m is 1;
n is 1;
p is 1;
Ar is R⁴-substituted aryl or R⁴-substituted heteroaryl;

Z is

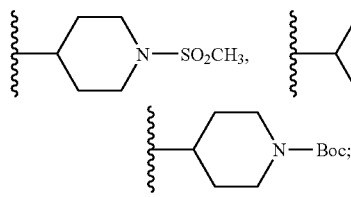

R¹ is halogen where said R¹ is substituted on the parent ring as follows

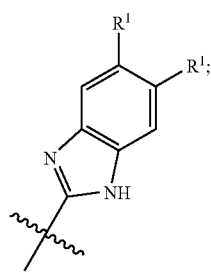

and
R⁴ is —CN or halogen.
23. The compound of claim 1 wherein the dashed line in

is —CH₂—;
m is 3;
n is 1;
p is 1;
Ar is R⁴-substituted aryl or R⁴-substituted heteroaryl;
Z is

R¹ is halogen or CF₃, where said R¹ is substituted on the parent ring as follows

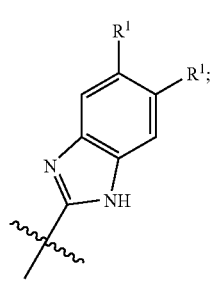

and
R⁴ is —CN or halogen.

24. A compound selected from the group consisting of

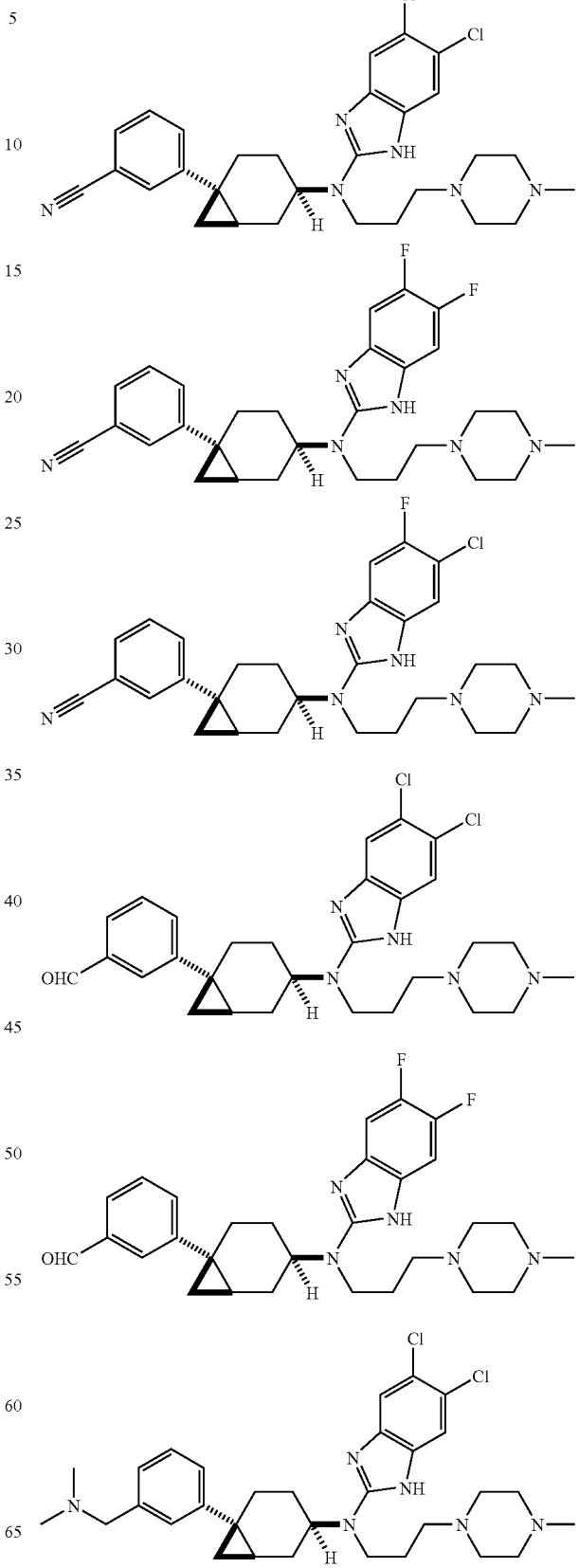

-continued
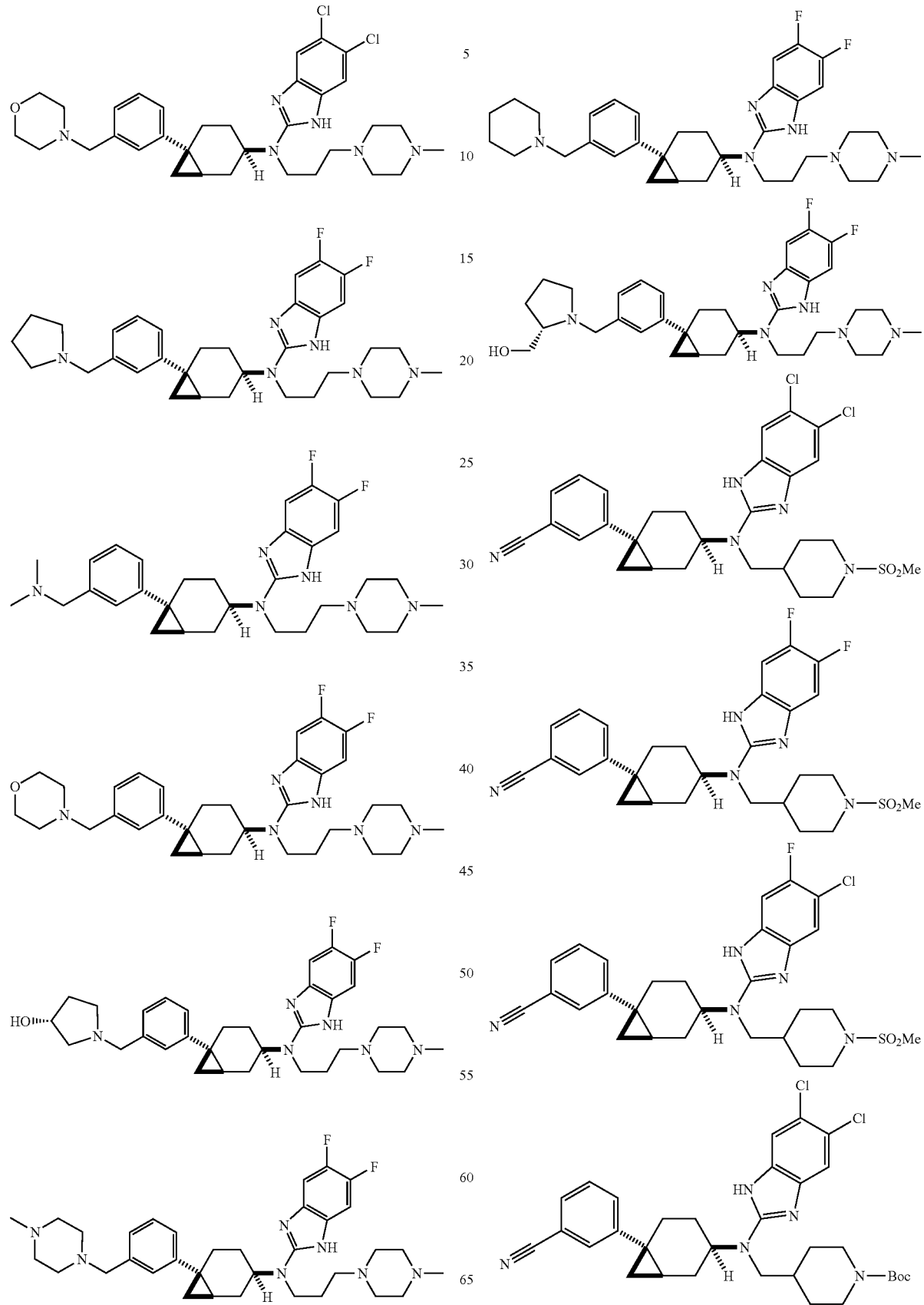
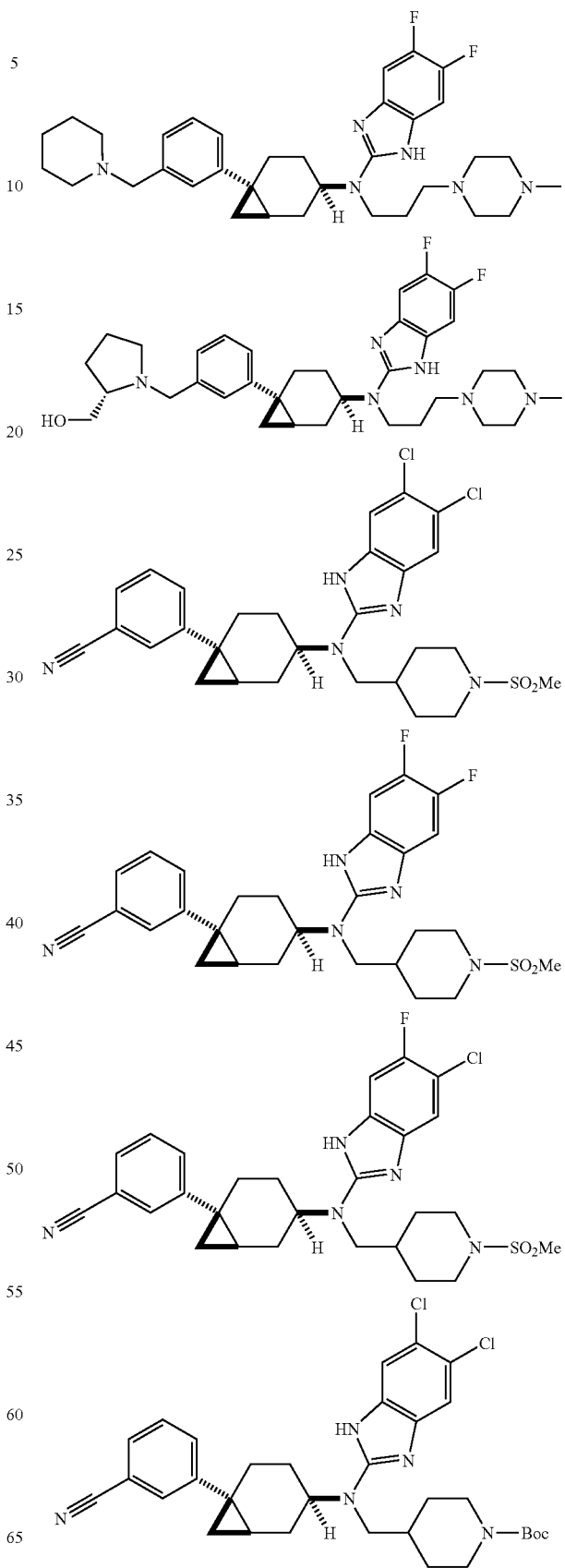

-continued
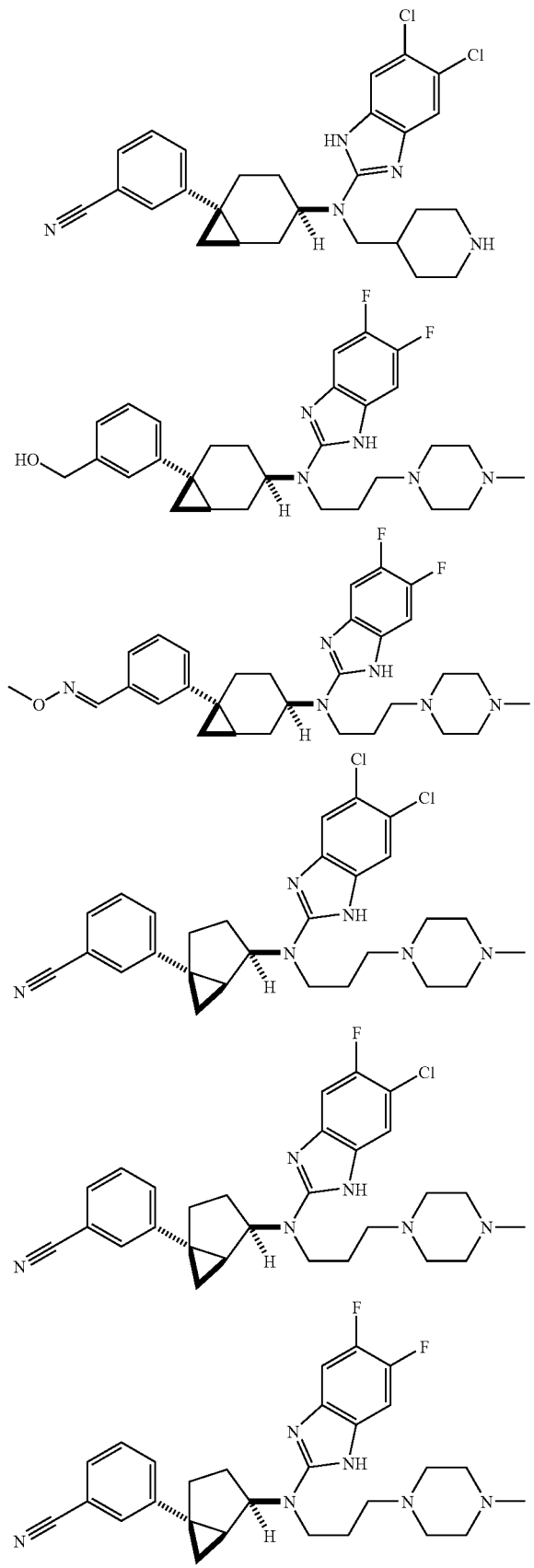
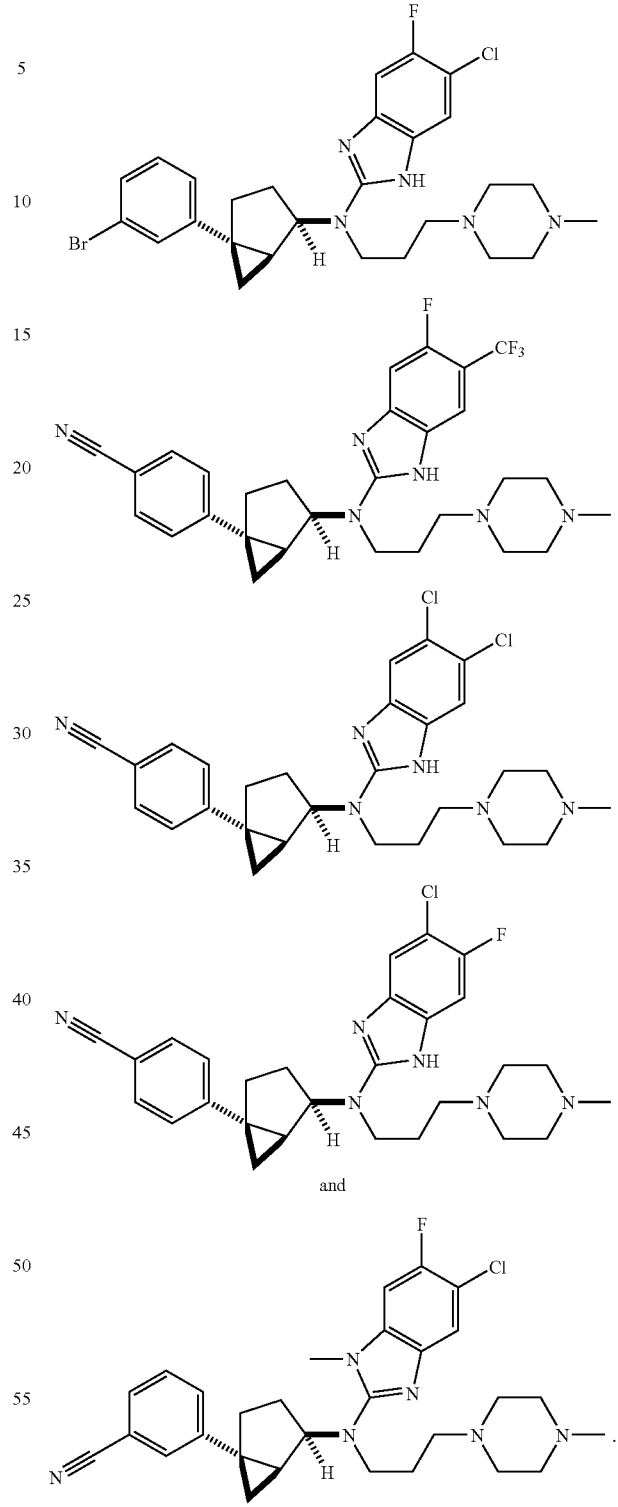
and
25. A method of treating a metabolic disorder, an eating disorder or diabetes comprising administering to a patient a therapeutically effective amount of at least one compound of claim 1 to a patient in need of such treatment.
26. A method of treating a metabolic disorder, an eating disorder or diabetes comprising administering to a patient a therapeutically effective amount of at least one compound of claim 24 to a patient in need of such treatment.

27. The method of claim 25 wherein said eating disorder is hyperphagia.

28. The method of claim 25 wherein said metabolic disorder is obesity.

29. A method of treating a disorder associated with obesity comprising administering to a mammal in need of such treatment a therapeutically effective amount of at least one compound of claim 1, or a pharmaceutically acceptable salt or solvate of said compound.

30. A method of treating a disorder associated with obesity comprising administering to a mammal in need of such treatment a therapeutically effective amount of at least one compound of claim 24, or a pharmaceutically acceptable salt or solvate of said compound.

31. The method of claim 29 wherein said disorder associated with obesity is at least one of type II diabetes, insulin resistance, hyperlipidemia or hypertension.

32. The method of claim 30 wherein said disorder associated with obesity is at least one of type II diabetes, insulin resistance, hyperlipidemia or hypertension.

33. A method of treating an eating disorder which comprises administering to a mammal in need of such treatment an amount of a first compound, said first compound being a compound of claim 1, or a pharmaceutically acceptable salt or solvate of said compound; and
    a second compound, said second compound being an antiobesity and/or anorectic agent selected from the group consisting of a $\beta_3$ agonist, a thryomimetic agent, an anorectic agent and an NPY antagonist;
    wherein the amounts of the first and second compounds result in a therapeutic effect.

34. A method of treating an eating disorder which comprises administering to a mammal in need of such treatment an amount of a first compound, said first compound being a compound of claim 24, or a pharmaceutically acceptable salt or solvate of said compound; and
    a second compound, said second compound being an antiobesity and/or anorectic agent selected from the group consisting of a $\beta_3$ agonist, a thryomimetic agent, an anorectic agent and an NPY antagonist;
    wherein the amounts of the first and second compounds result in a therapeutic effect.

35. A pharmaceutical composition which comprises a therapeutically effective amount of:
    a first compound, said first compound being a compound of claim 1, or a pharmaceutically acceptable salt or solvate of said compound;
    a second compound, said second compound being an antiobesity and/or anorectic agent selected from the group consisting of a $\beta_3$ agonist, a thryomimetic agent, an anorectic agent and NPY antagonist; and
    a pharmaceutically acceptable carrier.

36. A pharmaceutical composition which comprises a therapeutically effective amount of:
    a first compound, said first compound being a compound of claim 24, or a pharmaceutically acceptable salt or solvate of said compound;
    a second compound, said second compound being an antiobesity and/or anorectic agent selected from the group consisting of a $\beta_3$ agonist, a thryomimetic agent, an anorectic agent and NPY antagonist; and
    a pharmaceutically acceptable carrier.

37. A pharmaceutical composition which comprises a therapeutically effective amount of:
    a first compound, said first compound being a compound of claim 1, or a pharmaceutically acceptable salt or solvate of said compound;
    a second compound, said second compound selected from the group consisting of an aldose reductase inhibitor, a glycogen phosphorylase inhibitor, a sorbitol dehydrogenase inhibitor, a protein tyrosine phosphatase 1B inhibitor, a dipeptidyl protease inhibitor, insulin, an insulin mimetic, metformin, acarbose, troglitazone, rosaglitazone, pioglitazone, GW-1929, a sulfonylurea, glipazide, glyburide, and chlorpropamide; and
    a pharmaceutically acceptable carrier.

38. A pharmaceutical composition which comprises a therapeutically effective amount of:
    a first compound, said first compound being a compound of claim 24, or a pharmaceutically acceptable salt or solvate of said compound;
    a second compound, said second compound selected from the group consisting of an aldose reductase inhibitor, a glycogen phosphorylase inhibitor, a sorbitol dehydrogenase inhibitor, a protein tyrosine phosphatase 1B inhibitor, a dipeptidyl protease inhibitor, insulin, an insulin mimetic, metformin, acarbose, troglitazone, rosaglitazone, pioglitazone, GW-1929, a sulfonylurea, glipazide, glyburide, and chlorpropamide; and
    a pharmaceutically acceptable carrier.

39. A pharmaceutical composition comprising a therapeutically effective amount of at least one compound of claim 1 in combination with at least one pharmaceutically acceptable carrier.

40. A pharmaceutical composition comprising a therapeutically effective amount of at least one compound of claim 24 in combination with at least one pharmaceutically acceptable carrier.

41. A process for making a pharmaceutical composition comprising combining at least one compound of claim 1, and at least one pharmaceutically acceptable carrier.

42. A process for making a pharmaceutical composition comprising combining at least one compound of claim 24, and at least one pharmaceutically acceptable carrier.

* * * * *

UNITED STATES PATENT AND TRADEMARK OFFICE
CERTIFICATE OF CORRECTION

PATENT NO.       : 7,030,113 B2
APPLICATION NO.  : 10/954786
DATED            : April 18, 2006
INVENTOR(S)      : Thavalakulamgara K. Sasikumar and Duane A. Burnett It is certified that error appears in the above-identified patent and that said Letters Patent is hereby corrected as shown below:

Claim 7, col. 48, lines 20-24:    Please correct the formula:

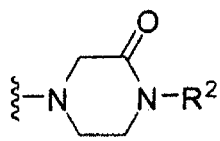

to

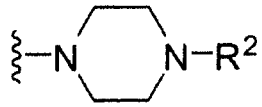

Signed and Sealed this

Twentieth Day of May, 2008

JON W. DUDAS
*Director of the United States Patent and Trademark Office*